(12) United States Patent
Campton et al.

(10) Patent No.: US 9,945,839 B2
(45) Date of Patent: *Apr. 17, 2018

(54) APPARATUS, SYSTEM, AND METHOD FOR COLLECTING A TARGET MATERIAL

(71) Applicant: RareCyte, Inc., Seattle, WA (US)

(72) Inventors: Daniel Campton, Seattle, WA (US); Joshua Nordberg, Bainbridge Island, WA (US); Steve Quarre, Seattle, WA (US); David Stewart, Seattle, WA (US); Ronald Seubert, Sammamish, WA (US)

(73) Assignee: RareCyte, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/351,293

(22) Filed: Nov. 14, 2016

(65) Prior Publication Data

US 2017/0059552 A1 Mar. 2, 2017

Related U.S. Application Data

(63) Continuation-in-part of application No. 14/610,522, filed on Jan. 30, 2015, now Pat. No. 9,539,570, which
(Continued)

(51) Int. Cl.
*G01N 33/49* (2006.01)
*B01L 3/00* (2006.01)
(Continued)

(52) U.S. Cl.
CPC .......... *G01N 33/491* (2013.01); *B01L 3/5021* (2013.01); *B01L 3/50215* (2013.01); *B01L 3/5635* (2013.01); *G01N 1/4077* (2013.01); *B01D 21/262* (2013.01); *B01L 9/50* (2013.01); *B01L 2200/026* (2013.01); *B01L 2300/046* (2013.01); *B01L 2300/0672* (2013.01); *B01L 2300/0851* (2013.01); *B01L 2400/0605* (2013.01); *B01L 2400/0683* (2013.01);
(Continued)

(58) Field of Classification Search
CPC ............... G01N 33/491; G01N 1/4077; G01N 2001/4083; B01L 3/5021; B01L 3/5635; B01L 3/50215; B01L 2300/046; B01L 2300/0851; B01L 2300/0672; B01L 2200/026; B01L 9/50; B01L 2400/0683; B01L 2400/0605; Y10T 436/25375; B01D 21/262
See application file for complete search history.

(56) References Cited

U.S. PATENT DOCUMENTS 3,661,265 A 5/1972 Greenspan
3,771,965 A 11/1973 Grams
(Continued)

FOREIGN PATENT DOCUMENTS

WO WO9712681 4/1997

*Primary Examiner* — Lore R Jarrett
(74) *Attorney, Agent, or Firm* — Shay Glenn LLP

(57) ABSTRACT

This disclosure is directed to an apparatus, system and method for retrieving a target material from a suspension. A system includes a displacement fluid, a collector, and a primary vessel. In another implementation, the system includes a processing vessel, a displacement fluid, a collector, and a primary vessel.

19 Claims, 28 Drawing Sheets

Related U.S. Application Data is a continuation-in-part of application No. 14/090,337, filed on Nov. 26, 2013, now abandoned, and a continuation-in-part of application No. 14/266,939, filed on May 1, 2014, now abandoned.

(60) Provisional application No. 61/935,457, filed on Feb. 4, 2014, provisional application No. 61/732,029, filed on Nov. 30, 2012, provisional application No. 61/745,094, filed on Dec. 21, 2012, provisional application No. 61/791,883, filed on Mar. 15, 2013, provisional application No. 61/818,301, filed on May 1, 2013, provisional application No. 61/869,866, filed on Aug. 26, 2013.

(51) Int. Cl.
*G01N 1/40* (2006.01)
*B01D 21/26* (2006.01)
*B01L 9/00* (2006.01)

(52) U.S. Cl.
CPC ............ *G01N 2001/4083* (2013.01); *Y10T 436/25375* (2015.01)

(56) References Cited

U.S. PATENT DOCUMENTS

| | | |
|---|---|---|
| 3,814,248 A | 6/1974 | Lawhead |
| 3,873,271 A | 3/1975 | Young et al. |
| 3,879,295 A | 4/1975 | Glover et al. |
| 4,037,464 A | 7/1977 | Wenander |
| 4,187,861 A * | 2/1980 | Heffernan ............ B01L 3/5082 422/913 |
| 4,436,631 A | 3/1984 | Graham, Jr. et al. |
| 4,464,254 A | 8/1984 | Dojki et al. |
| 4,644,807 A | 2/1987 | Mar |
| 4,925,627 A | 5/1990 | Johnson |
| 4,927,605 A | 5/1990 | Dorn et al. |
| 5,019,243 A | 5/1991 | McEwan et al. |
| 5,248,480 A | 9/1993 | Greenfield |
| 5,254,312 A | 10/1993 | Staebler et al. |
| 5,282,981 A * | 2/1994 | Adams ............... B01L 3/50215 210/516 |
| 5,286,453 A | 2/1994 | Pope |
| 5,393,674 A | 2/1995 | Levine et al. |
| 5,646,004 A * | 7/1997 | Van Vlasselaer ..... B01L 3/5021 210/781 |
| 5,714,125 A | 2/1998 | Sagstetter |
| 5,888,831 A | 3/1999 | Gautsch |
| 5,910,289 A | 6/1999 | Sagstetter |
| 6,221,655 B1 | 4/2001 | Fung et al. |
| 7,456,024 B2 | 11/2008 | Dahm et al. |
| 7,524,641 B2 | 4/2009 | Jurgensen et al. |
| 7,959,866 B2 | 6/2011 | Crawford et al. |
| 2003/0208162 A1 | 11/2003 | Crawford |
| 2004/0025603 A1 | 2/2004 | Liseo et al. |
| 2004/0025935 A1 | 2/2004 | Liseo et al. |
| 2005/0014273 A1 | 1/2005 | Dahm et al. |
| 2008/0025877 A1 | 1/2008 | Alley |
| 2008/0284164 A1 | 11/2008 | Kerin et al. |
| 2009/0100915 A1 | 4/2009 | Shiraki et al. |
| 2010/0093551 A1 | 4/2010 | Montagu |
| 2010/0120596 A1 | 5/2010 | Froman et al. |
| 2010/0155319 A1 | 6/2010 | Felix et al. |
| 2011/0033925 A1 | 2/2011 | Duffy et al. |
| 2011/0251041 A1 | 10/2011 | Chavarria et al. |
| 2014/0087360 A1 | 3/2014 | Woodside |

* cited by examiner

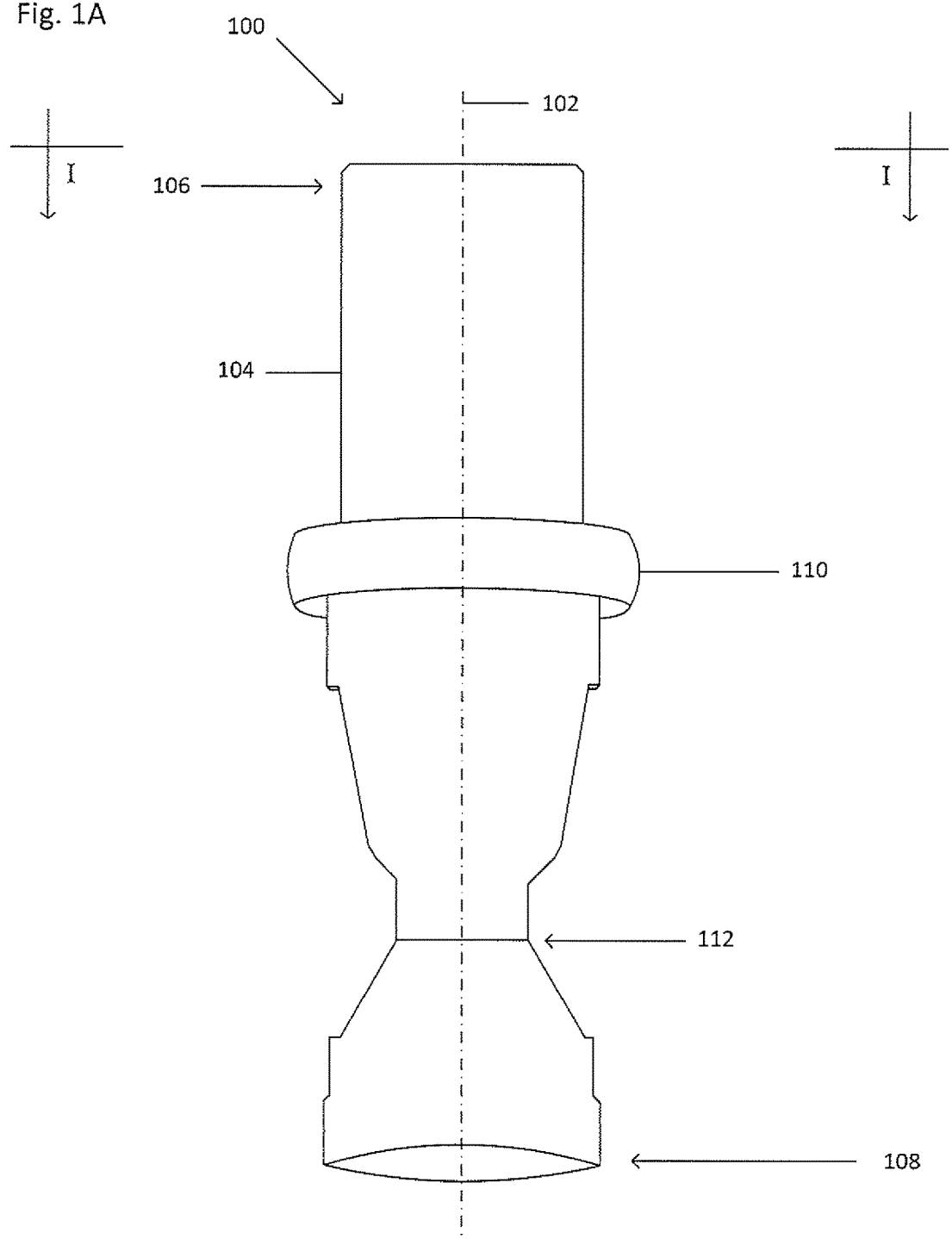

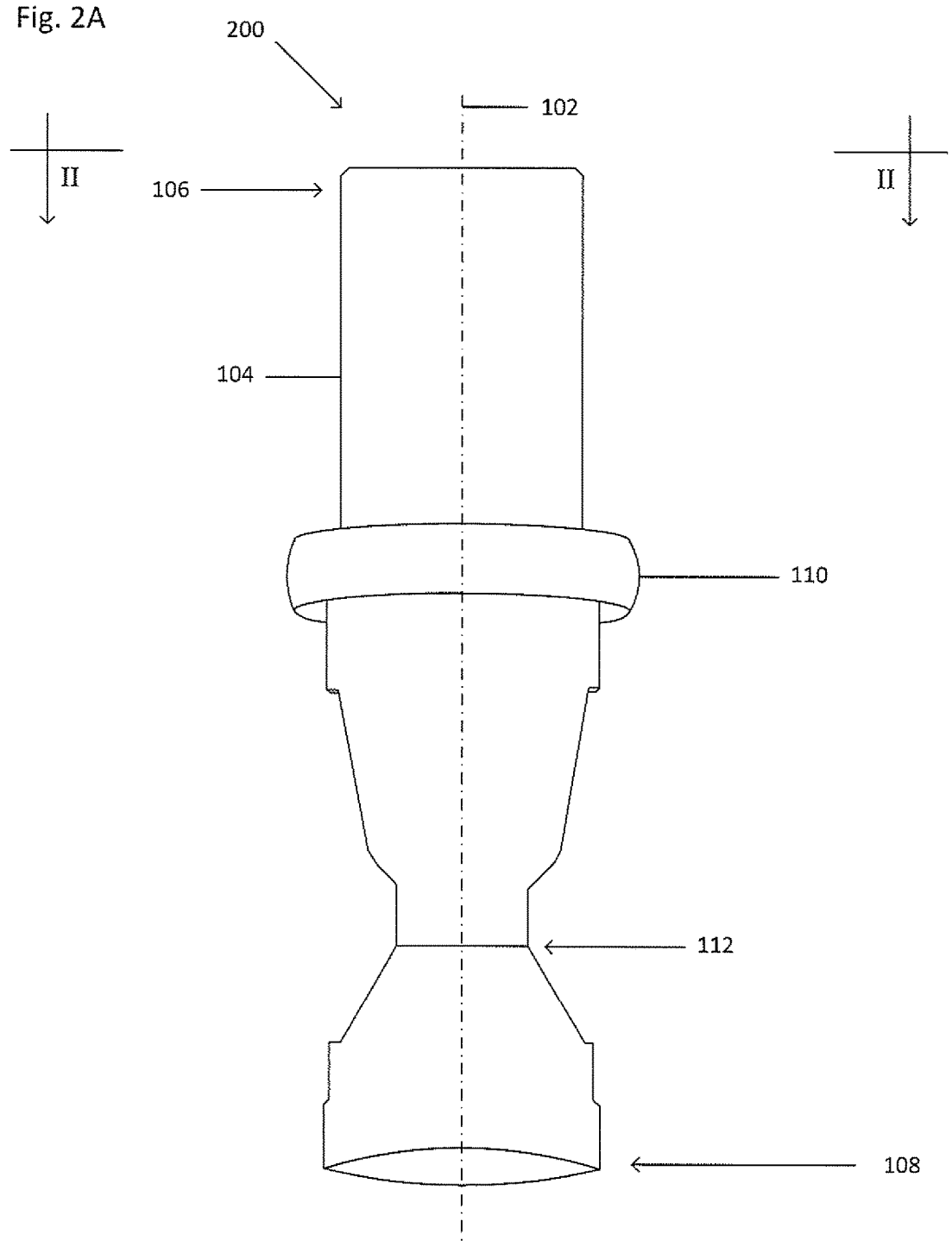

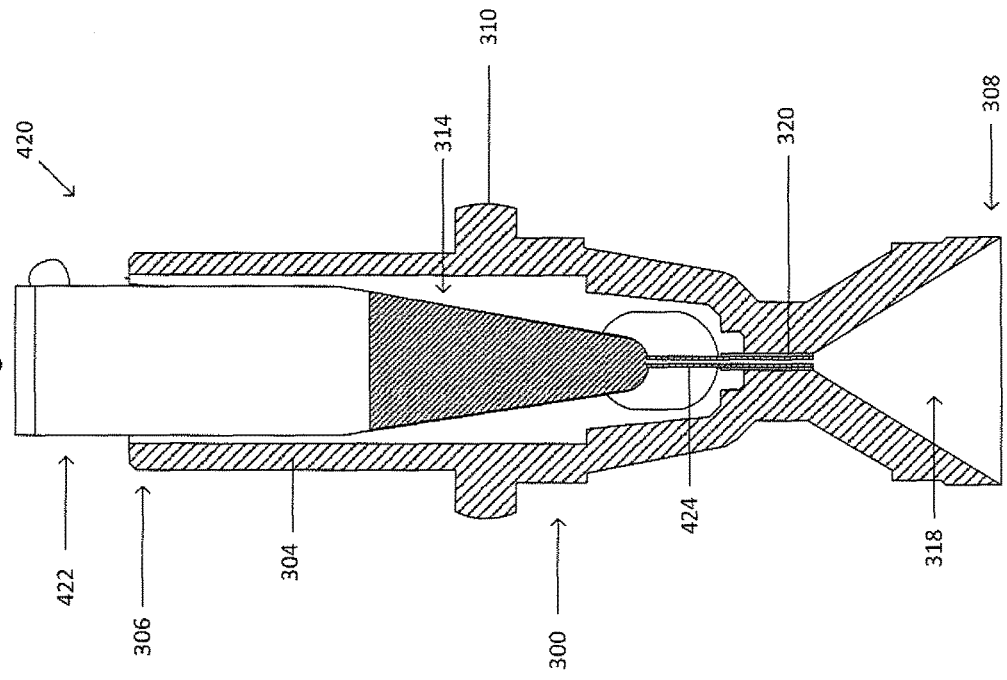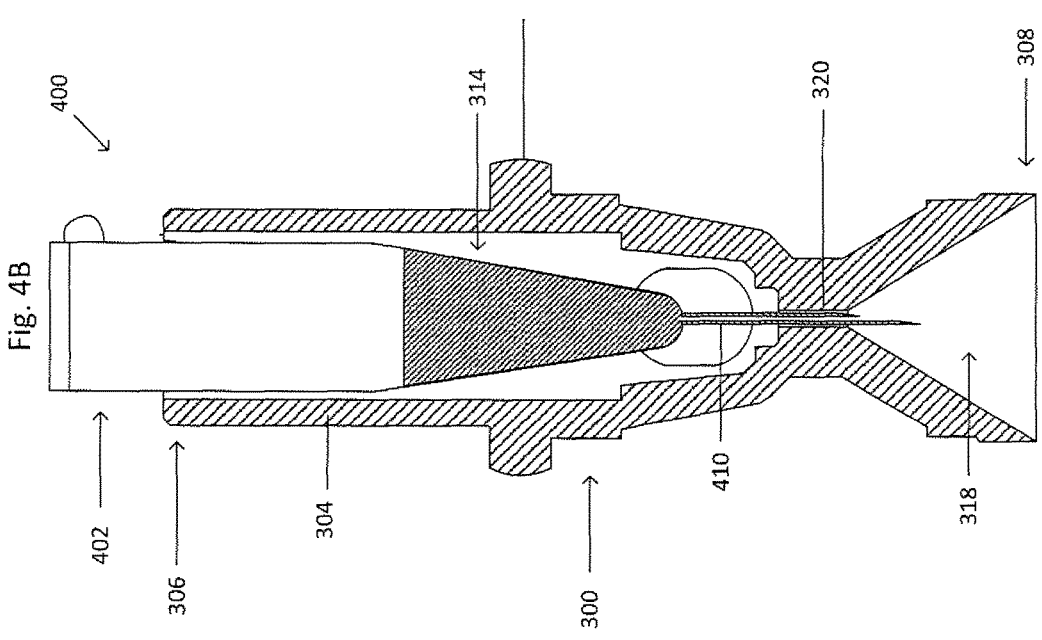

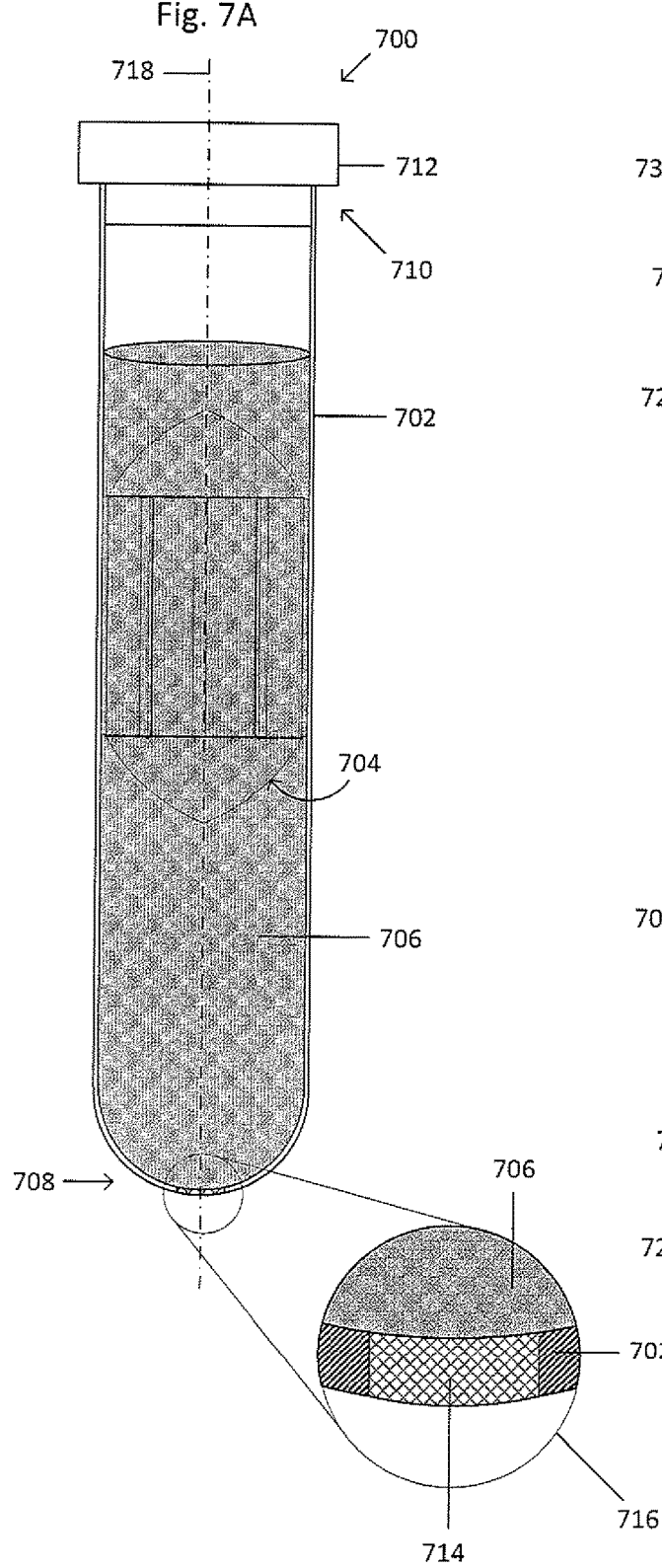
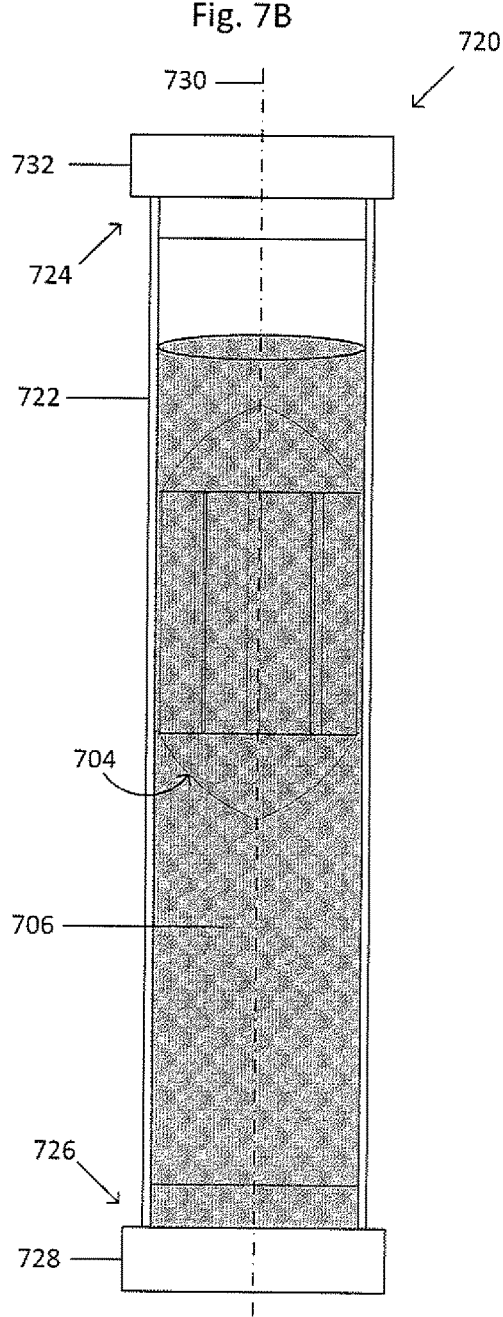
Fig. 7A
Fig. 7B

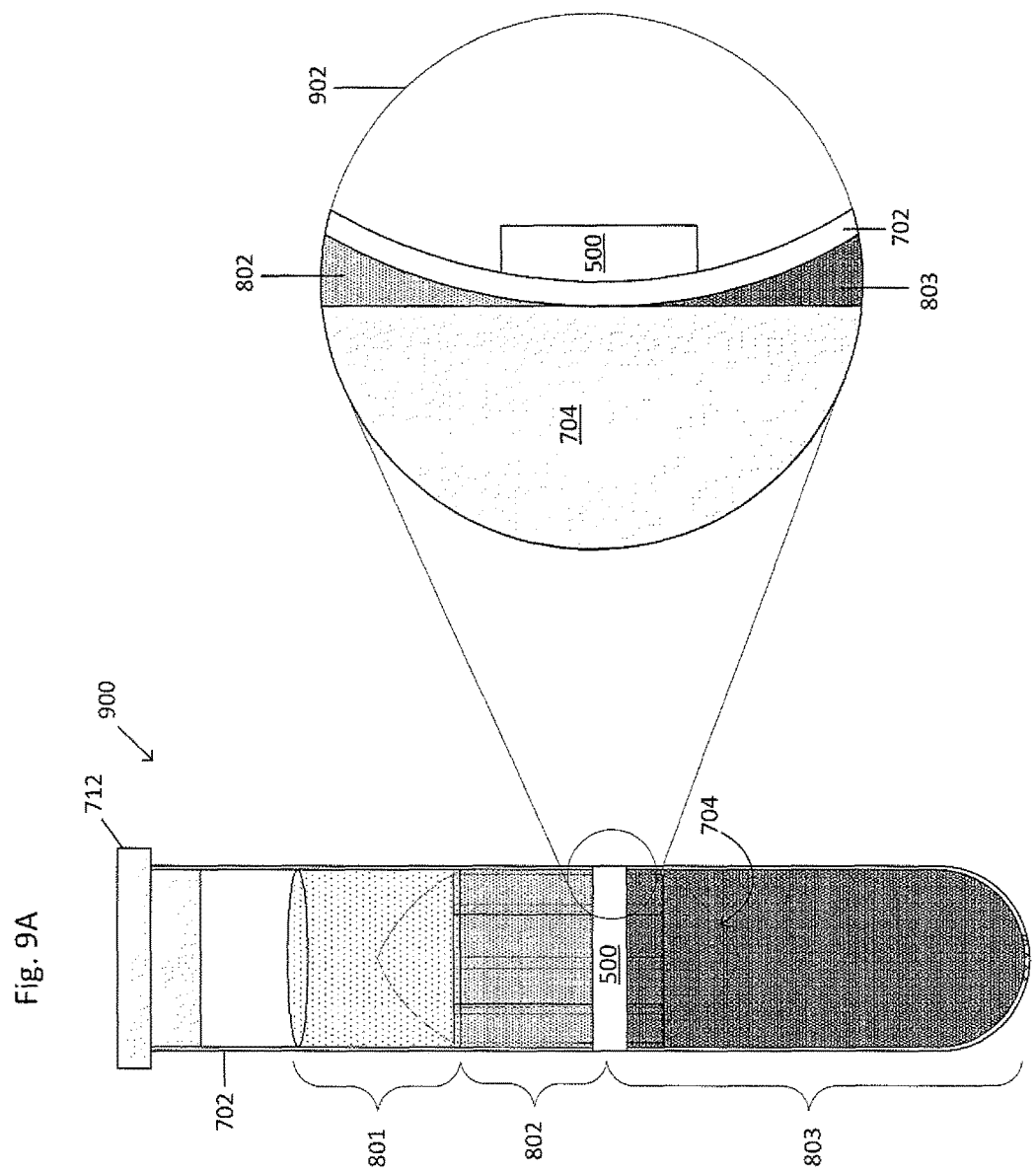

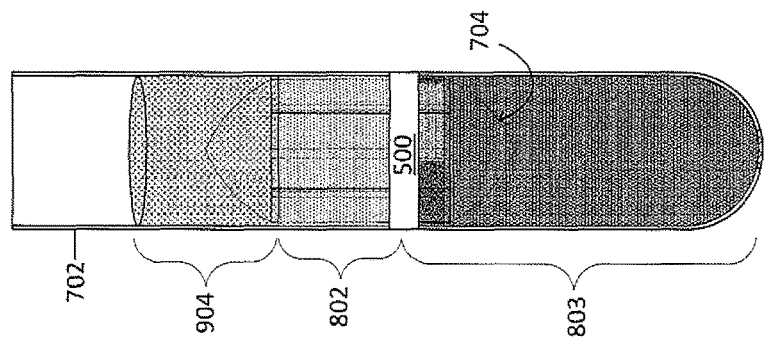
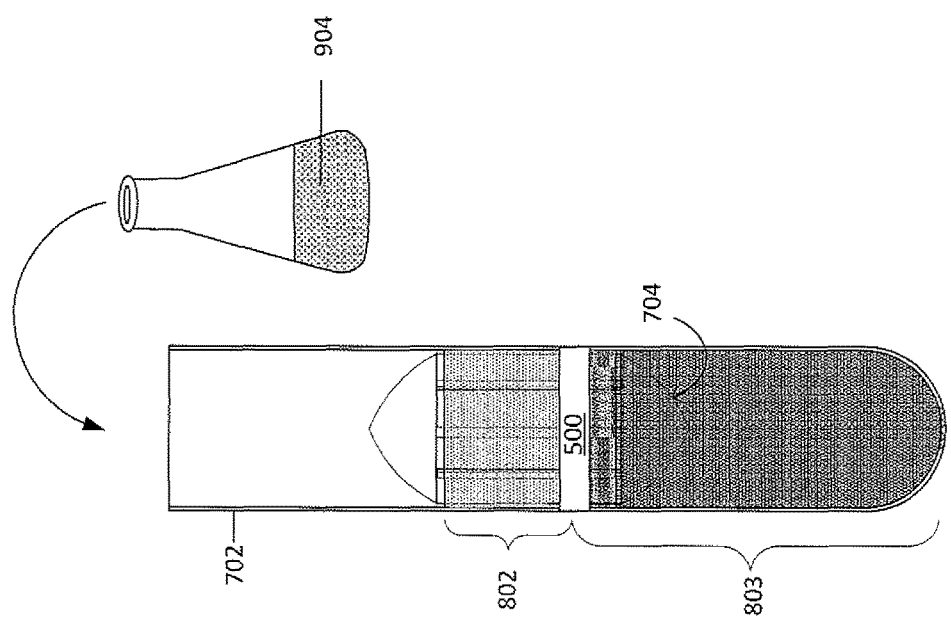

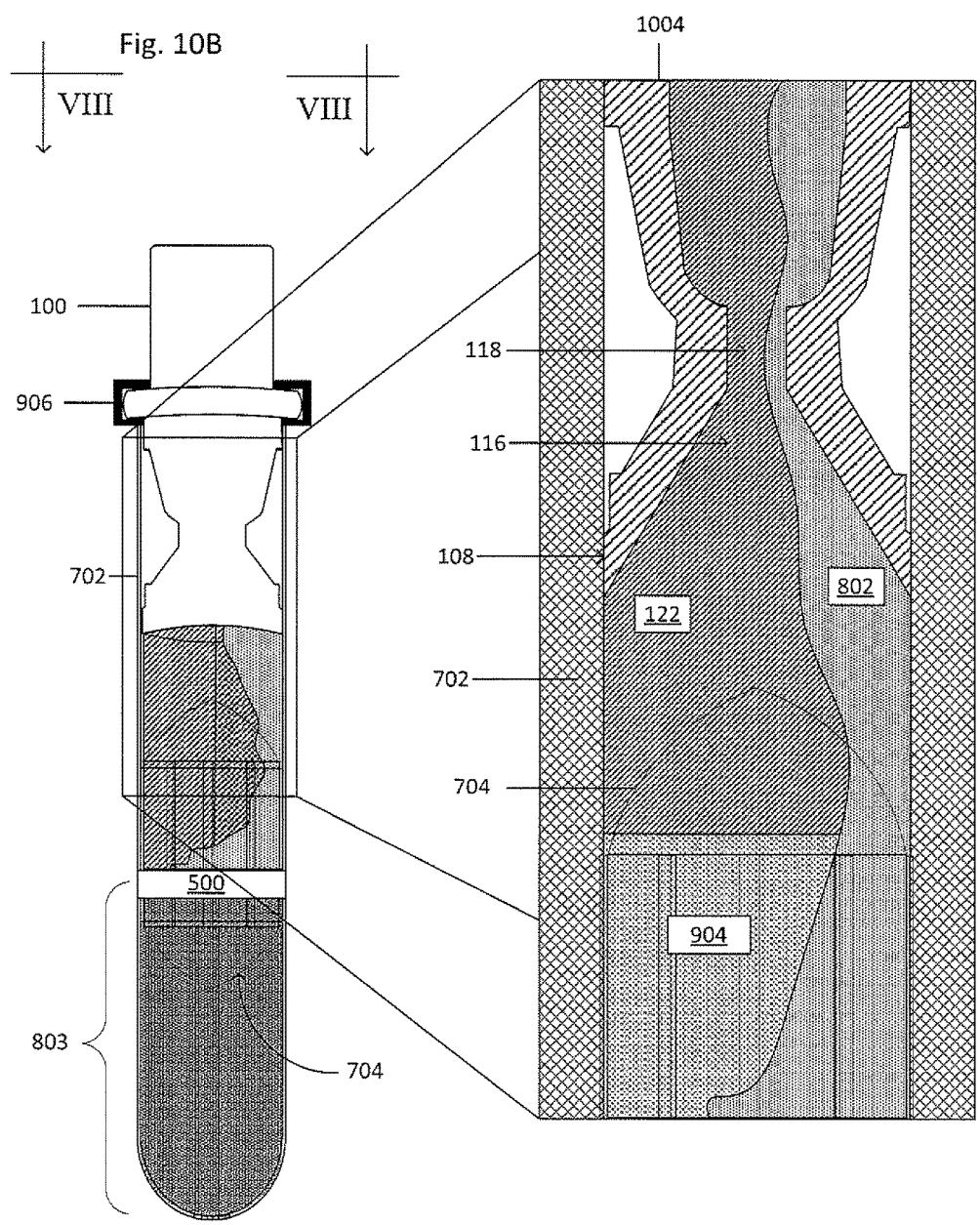

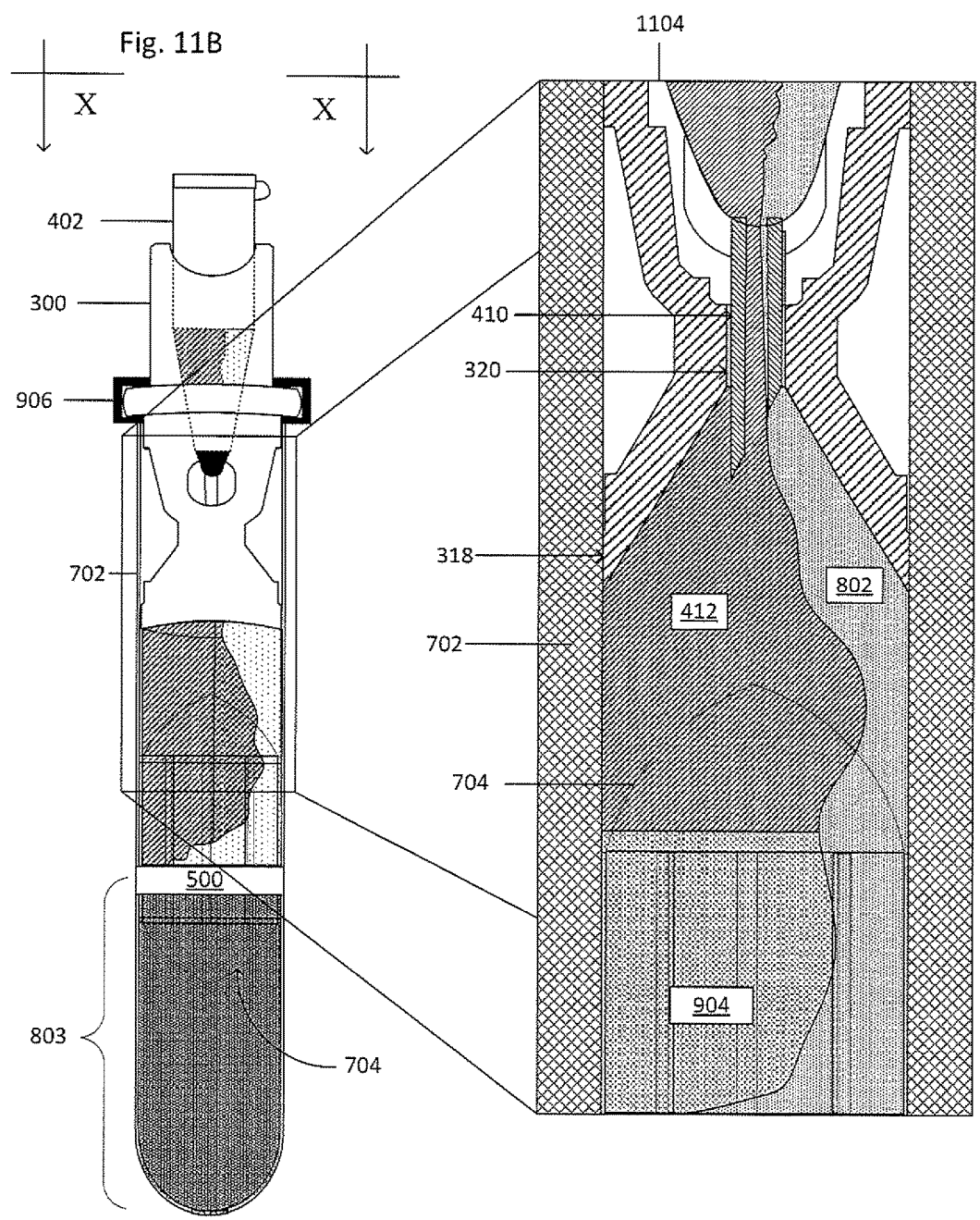

APPARATUS, SYSTEM, AND METHOD FOR COLLECTING A TARGET MATERIAL

CROSS-REFERENCE TO A RELATED APPLICATION

This application is a continuation-in-part of application Ser. No. 14/610,522, filed Jan. 30, 2015, which claims the benefit of Provisional Application No. 61/935,457, filed Feb. 4, 2014, and which is a continuation-in-part of Application Ser. No. 14/090,337, filed Nov. 26, 2013, (now abandoned) which claims the benefit of Provisional Application No. 61/732,029, filed Nov. 30, 2012; Provisional Application No. 61/745,094, filed Dec. 21, 2012; Provisional Application No. 61/791,883, filed Mar. 15, 2013; Provisional Application No. 61/818,301, filed May 1, 2013; and Provisional Application No. 61/869,866, filed Aug. 26, 2013; and which is also a continuation-in-part of application Ser. No. 14/266,939, filed May 1, 2014, (now abandoned) which claims the benefit of Provisional Application No. 61/818,301, filed May 1, 2013, Provisional Application No. 61/869,866, filed Aug. 26, 2013, and Provisional Application No. 61/935,457, filed Feb. 4, 2014.

TECHNICAL FIELD

This disclosure relates generally to density-based fluid separation and, in particular, to retrieving a target material from a suspension.

BACKGROUND

Materials of interest that occur in a suspension with very low concentrations are especially difficult if not impossible to detect and analyze using many existing techniques. Consider, for instance, circulating tumor cells ("CTCs"), which are cancer cells that have detached from a tumor, circulate in the bloodstream, and may be regarded as seeds for subsequent growth of additional tumors (i.e., metastasis) in different tissues. The ability to accurately detect and analyze CTCs is of particular interest to oncologists and cancer researchers. However, CTCs occur in very low numbers in peripheral whole blood samples. For instance, a 7.5 ml sample of peripheral whole blood sample that contains as few as 5 CTCs is considered clinically relevant for the diagnosis and treatment of a cancer patient. In other words, detecting 5 CTCs in a 7.5 ml blood sample is equivalent to detecting 1 CTC in a background of about 10 billion red and white blood cells, which is extremely time consuming, costly and difficult to accomplish using blood film analysis.

As a result, practitioners, researchers, and those working with suspensions continue to seek systems and methods for accurate analysis of suspensions for the presence or absence rare materials of interest.

DESCRIPTION OF THE DRAWINGS

FIGS. 1A-1B show an example collector.
FIGS. 2A-2B show an example collector.
FIGS. 4A-4C show an example collector-processing vessel system.
FIGS. 7A-7B show example float and primary vessel systems.
FIGS. 9A-9H show an example system retrieving a target material.
FIGS. 10A-10C show an example system retrieving a target material.
FIGS. 11A-11C show an example system retrieving a target material.

DETAILED DESCRIPTION

This disclosure is directed to an apparatus, system and method for retrieving a target material from a suspension. A system includes a displacement fluid, a collector, and a primary vessel. In another implementation, the system includes a processing vessel, a displacement fluid, a collector, and a primary vessel.

Collector

Figure 1B:
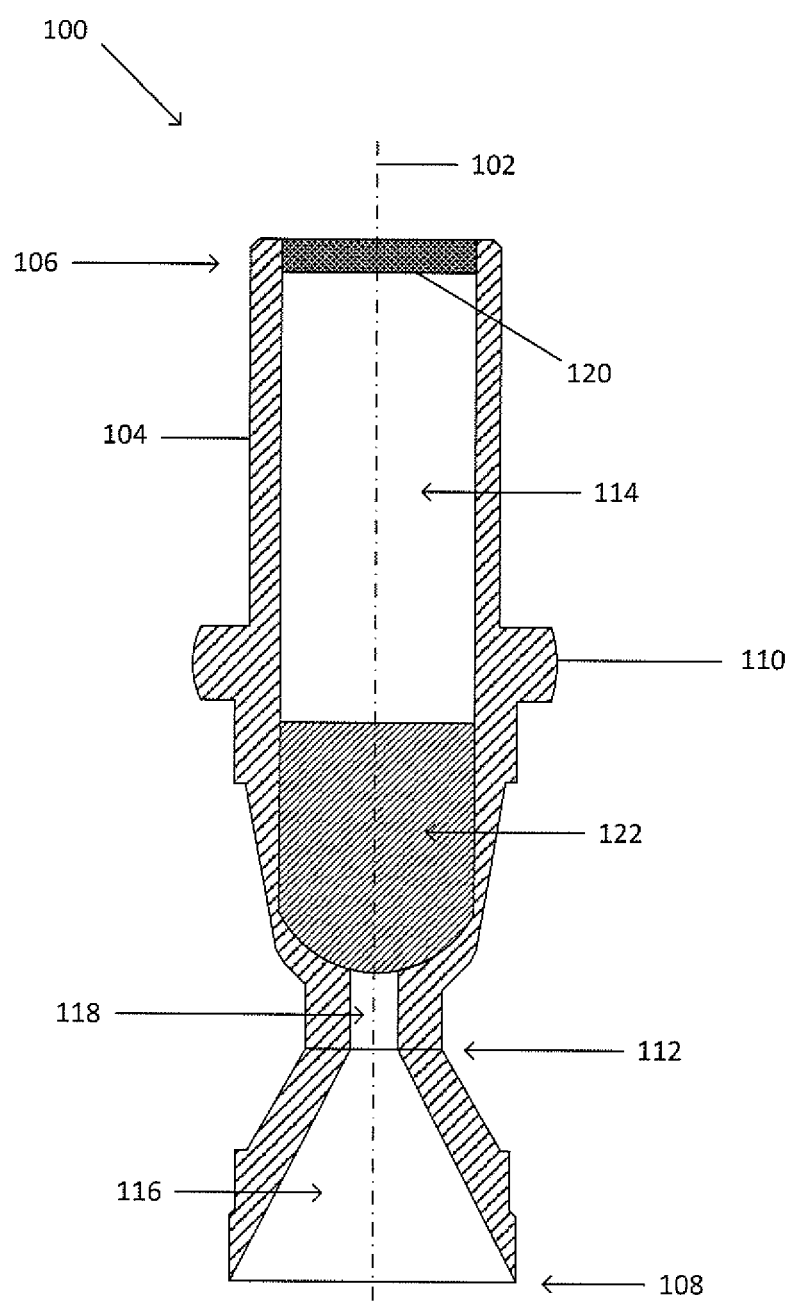

FIG. 1A shows an isometric view of a collector 100. FIG. 1B shows a cross-section view of the collector 100 taken along the line I-I. Dot-dashed line 102 represents the central or highest-symmetry axis of the collector 100. The collector 100 may be sized and shaped to fit within a primary vessel containing or capable of holding a suspension, the suspension suspected of including a target material.

The collector 100 includes the main body 104 which includes a first end 106 and a second end 108. The main body 104 may be any appropriate shape, including, but not limited to, cylindrical, triangular, square, rectangular, or the like. The collector 100 also includes a concave opening 116 extending from the second end 108 into the main body 104. The concave opening 116 channels the target material beneath the inner bore 118 which is connected to and in fluid communication with an apex of the concave opening 116. The apex of the concave opening 116 may have a smaller, equal, or larger diameter than the mouth of the concave opening 116. The concave opening 116 may be formed by a tapered wall that may be straight, curvilinear, arcuate, or the like.

The collector 100 may form a seal with an inner wall of the primary vessel to inhibit any portion of the suspension from being located between a sidewall of the primary vessel and a main body 104 of the collector 100. The seal may be formed by an interference fit, a grease (such as vacuum grease), an adhesive, an epoxy, by bonding (such as by thermal bonding), by welding (such as by ultrasonic welding), by clamping (such as with a ring or clamp), an insert (such as an O-ring or a collar) that fits between the second end 108 and the inner wall of the primary vessel, or the like. The main body 104 may be any appropriate shape, including, but not limited to, cylindrical, triangular, square, rectangular, or the like.

The collector 100 includes an inner bore 118 extending from the apex of the concave opening 116 to the cavity 114, thereby putting the concave opening 116 and the cavity 114 in fluid communication with one another. The inner bore 118 is sized and shaped—along with the surface tensions of the respective fluids above and/or below the inner bore 118—such that before and after centrifugation fluid cannot and does not pass between the cavity 108 and the concave opening 116. However, during centrifugation, the force exerted on the respective fluids permit fluid to flow between the cavity 108 and the concave opening 116. In other words, the inner bore 118 permits for fluid flow between the second end 108 and the cavity when undergoing centrifugation, while preventing fluid flow between the second end 108 and the cavity when not undergoing centrifugation. The force applied by centrifugation may include, but is not limited to, 2 g, 5 g, 10 g, 100 g, 1000 g, 1000 g, 2500 g, 3000 g, 5000 g, or 10000 g, where g is the force of gravity.

The collector 100 may also include a lid 120 at or near the first end 106 to seal, whether temporarily or permanently, an opening within the first end 106, thereby inhibiting fluids from leaking out of the opening in the first end 106. The opening may be in fluid communication with the cavity 108. The lid 120 may removable, or temporarily or permanently affixed. The lid 120 may be puncturable and resealable or puncturable and non-resealable (e.g. a foil lid).

The main body 104 may include a break-point 112 where a inner bore 118 meets an apex of a concave opening 116 within the second end 108. The break-point 112 permits the cavity 114 and the inner bore 118 to be separated from the concave opening 116 of the second end 108 so that the target material may be removed and retained in a single vessel for subsequent processing while maintaining the seal between the second end 108 and the primary vessel (not shown).

The collector 100 may include a shoulder 110, which extends circumferentially around the main body 104. The shoulder 110 may be larger than the inner diameter of the primary vessel so as to rest on the open end of the primary vessel and, upon applying a lock ring (not shown) to the outside of the primary vessel and the shoulder 110, to inhibit movement of the collector 100 relative to the primary vessel. The lock ring (not shown) applies pressure to the primary vessel along the shoulder 110. The lock ring may be a two-piece ring, a one piece ring wrapping around the full circumference of the primary vessel, or a one piece ring wrapping around less than the full circumference of the primary vessel, such as one-half (½), five-eighths (⅝), two-thirds (⅔), three-quarters (¾), seven-eighths (⅞), or the like. Alternatively, the shoulder 110 may fit within the primary vessel.

The collector 100 also includes a displacement fluid 122 having a density greater than the density of at least a portion of the target material of the suspension (the density may be greater than the density of a subset of suspension fractions or all of the suspension fractions). The displacement fluid 122 displaces the target material, such that when the collector 100 inserted into the primary vessel (not shown), and the collector and primary vessel undergo centrifugation, the displacement fluid 122 flows out of the collector 100 and into the primary vessel, and, through displacement, such as through buoyant displacement (i.e. lifting a material upwards), pushes the target material through the inner bore 118, which is open due to centrifugation, and into the cavity 114.

Figure 2B:
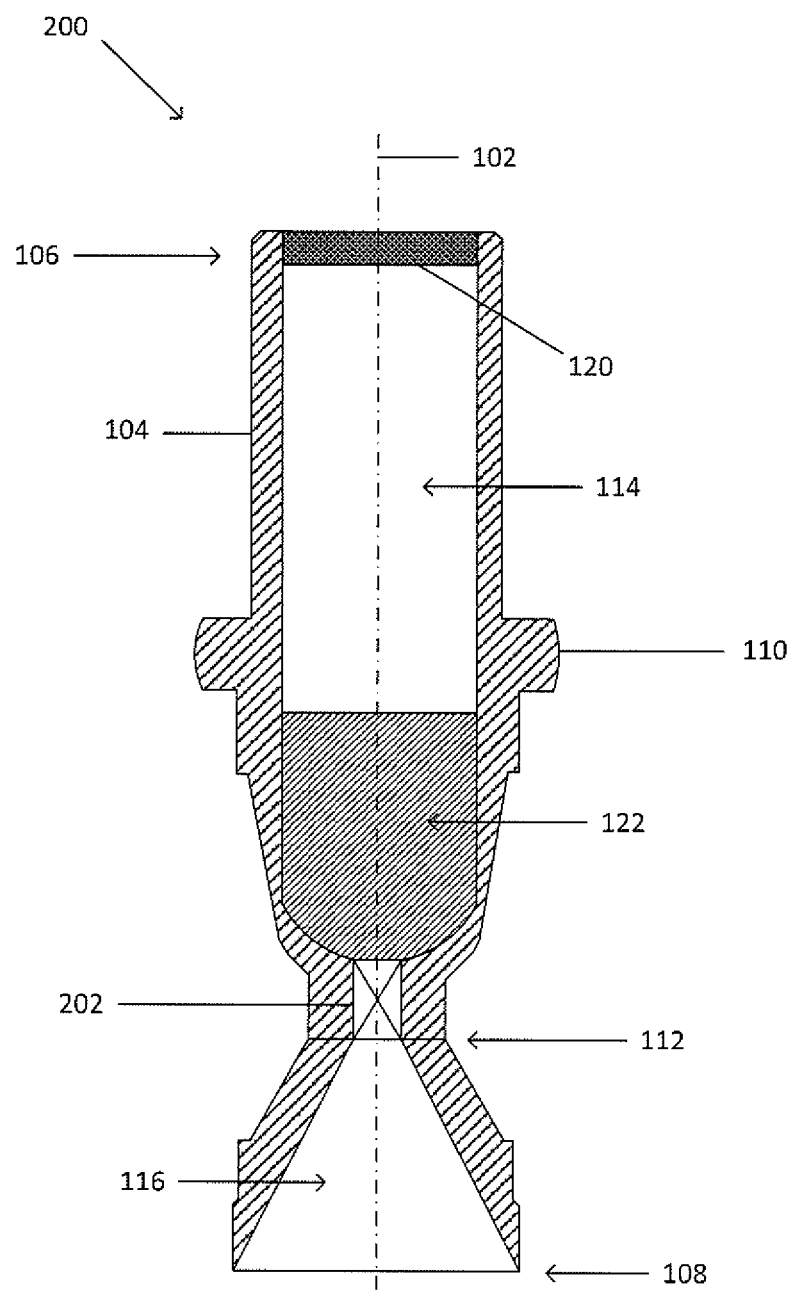

FIG. 2A shows an isometric view of a collector 200. FIG. 2B shows a cross-section view of the collector 200 taken along the line II-II. The collector 200 is similar to the collector 100 except that the collector 200 has a valve 202 instead of the inner bore 118 of the collector 100.

When undergoing centrifugation, the valve 202 opens to permit fluid flow between the second end 108 and a cavity 114 in the main body 204. When not undergoing centrifugation, the valve 202 is closed to inhibit fluid flow between the second end 108 and the cavity 114. The valve 202 permits for fluid between the second end 108 and the cavity 114 when undergoing centrifugation, while preventing fluid flow between the second end 108 and the cavity 114 when not undergoing centrifugation. The valve 202 may include but is not limited to a ball check valve, a diaphragm check valve, a swing check valve, a tilting disk check valve, a lift check valve, and a duckbill valve. Alternatively, the valve 202 is closed when the centrifugal forces are less than or equal to a predetermined amount and the valve 202 is open when the centrifugal forces are greater than or equal to a predetermined amount. The predetermined amount may include, but is not limited to, 2 g, 5 g, 10 g, 100 g, 1000 g, 2000 g, 2500 g, 3000 g, 5000 g, or 10000 g, where g is the force of gravity.

Figure 3A:
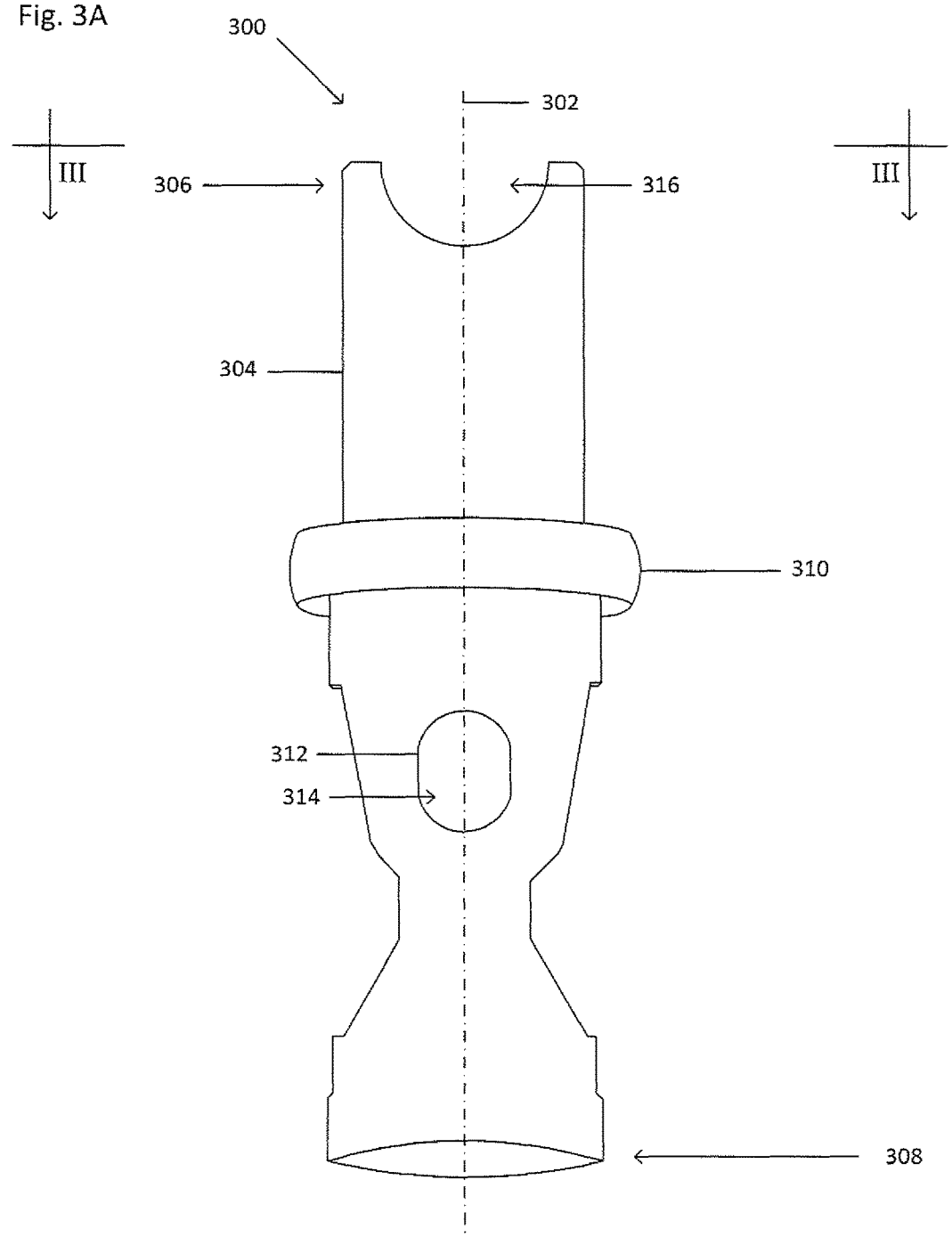
FIGS. 3A-3B show an example collector.
Figure 3B:
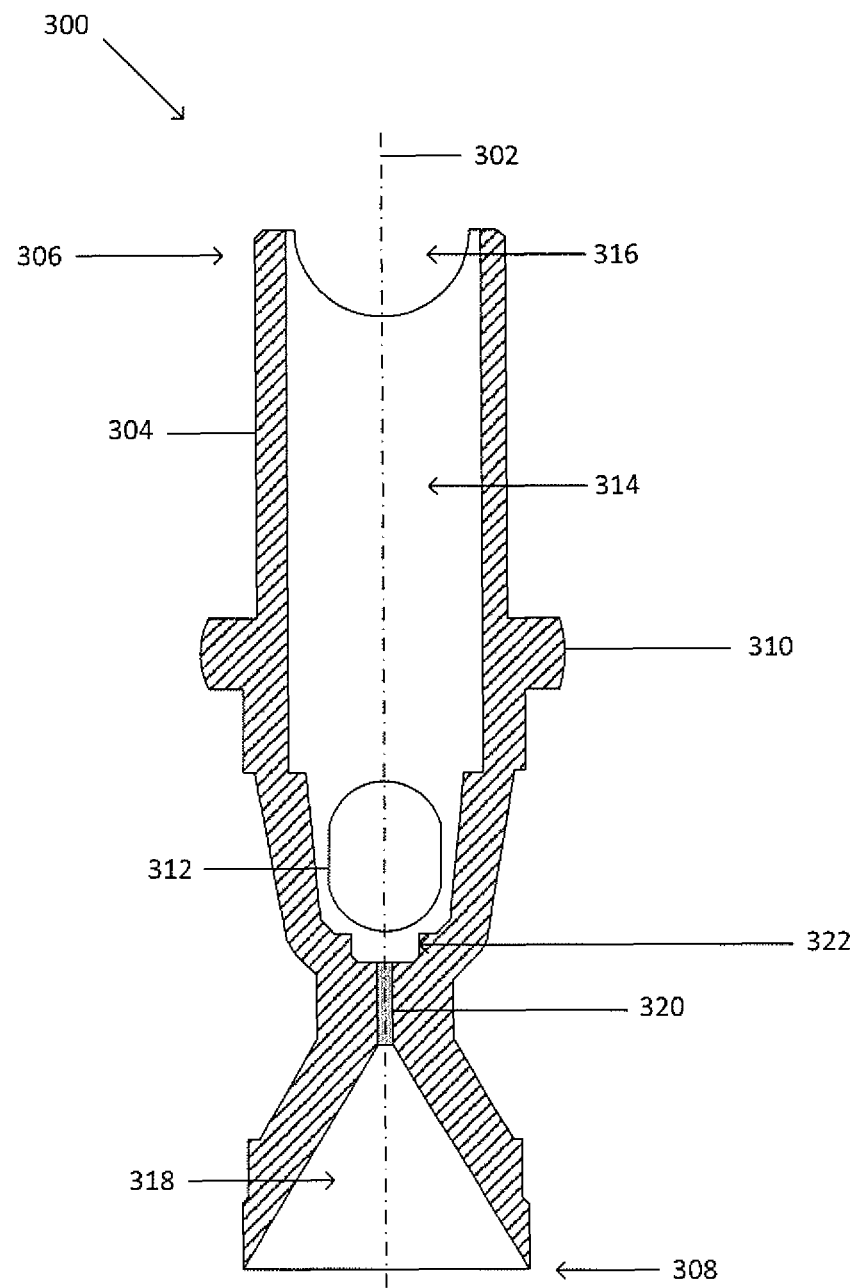

FIG. 3A shows an isometric view of a collector 300. FIG. 3B shows a cross-section view of the collector 300 taken along the line shown in FIG. 3A. Dot-dashed line 302 represents the central or highest-symmetry axis of the collector 300. The collector 300 includes a main body 304 having a first end 306 and a second end 308. The first end 306 includes a cavity 314 dimensioned to accept and hold at least a portion of the processing vessel (not shown). The cavity 312 may have a tapered or stepped bottom end 322 on which a processing vessel (not shown) may rest. The first end 306 may also include at least one cut-out 316 to permit proper grip of the processing vessel (not shown) for insertion and removal. The collector 300 also includes a concave opening 318 extending from the second end 308 into the main body 304. The concave opening 318 channels the target material beneath a septum 320 which inhibits fluid flow or fluid communication between the concave opening 318 and the cavity 314. The apex of the concave opening 318 may have a smaller, equal, or larger diameter than the mouth of the concave opening 318. The concave opening 318 may be formed by a tapered wall that may be straight, curvilinear, arcuate, or the like.

The septum 320 extends from the apex of the concave opening 318 to cavity 314. The septum 320 may be composed of re-sealable rubber or other suitable re-sealable material that can be repeatedly punctured with a needle or other sharp implement to access the material within the concave opening 318. The septum 320 may be inserted into the collector 300 such that a seal is maintained between the septum 320 and the main body 302, such as by an interference fit. Alternatively, the septum 320 can be formed in the main body 304 of the collector 300 using heated liquid rubber that can be shaped while warm or hot and hardens as the rubber cools. An adhesive, such as a polymer-based adhesive, an epoxy, a contact adhesive or any other suitable material for bonding or creating a thermal bond, may be used to attach a septum 320 to the main body 304. Alternatively, the septum 320 may be injected into the main body 304. Alternatively, the septum 320 may be thermally bonded to the main body 304.

The collector 300 may include a shoulder 310, which extends circumferentially around the main body 304. The shoulder 310 may be larger than the inner diameter of the primary vessel so as to rest on the open end of the primary vessel and, upon applying a lock ring (not shown) to the outside of the primary vessel and the shoulder 310, to inhibit movement of the collector 300 relative to the primary vessel. The lock ring (not shown) applies pressure to the primary vessel along the shoulder 310. The lock ring may be a two-piece ring, a one piece ring wrapping around the full circumference of the primary vessel, or a one piece ring wrapping around less than the full circumference of the primary vessel, such as one-half (½), five-eighths (⅝), two-thirds (⅔), three-quarters (¾), seven-eighths (⅞), or the like. Alternatively, the shoulder 310 may fit within the primary vessel. Alternatively, the shoulder 310 may be a clip, such that the shoulder 310 may include a catch into which the primary vessel may be inserted to inhibit movement of the collector 300 relative to the primary vessel. Alternatively, the shoulder 310 may form an interference fit with the inner wall of the primary vessel around which a seal ring may be placed.

The collector 300 may include at least one window 312 to access the cavity 314 through a wall of the main body 304. The at least one window 312 permits an operator to confirm proper placement of the processing vessel (not shown) within the cavity 314.

A seal may be formed between the second end 308 and an inner wall of the primary vessel to maintain a fluid-tight sealing engagement before, during, and after centrifugation and to inhibit any portion of the suspension flowing between an inner wall of the primary vessel and the main body 304 of the collector 300. The seal may be formed by an interference fit, a grease (such as vacuum grease), an adhesive, an epoxy, by bonding (such as thermal bonding), by welding (such as ultrasonic welding), clamping (such as with a ring or clamp), an insert (such as an O-ring or a collar) that fits between the second end 208 and the inner wall of the primary vessel, or the like.

Figure 4A:
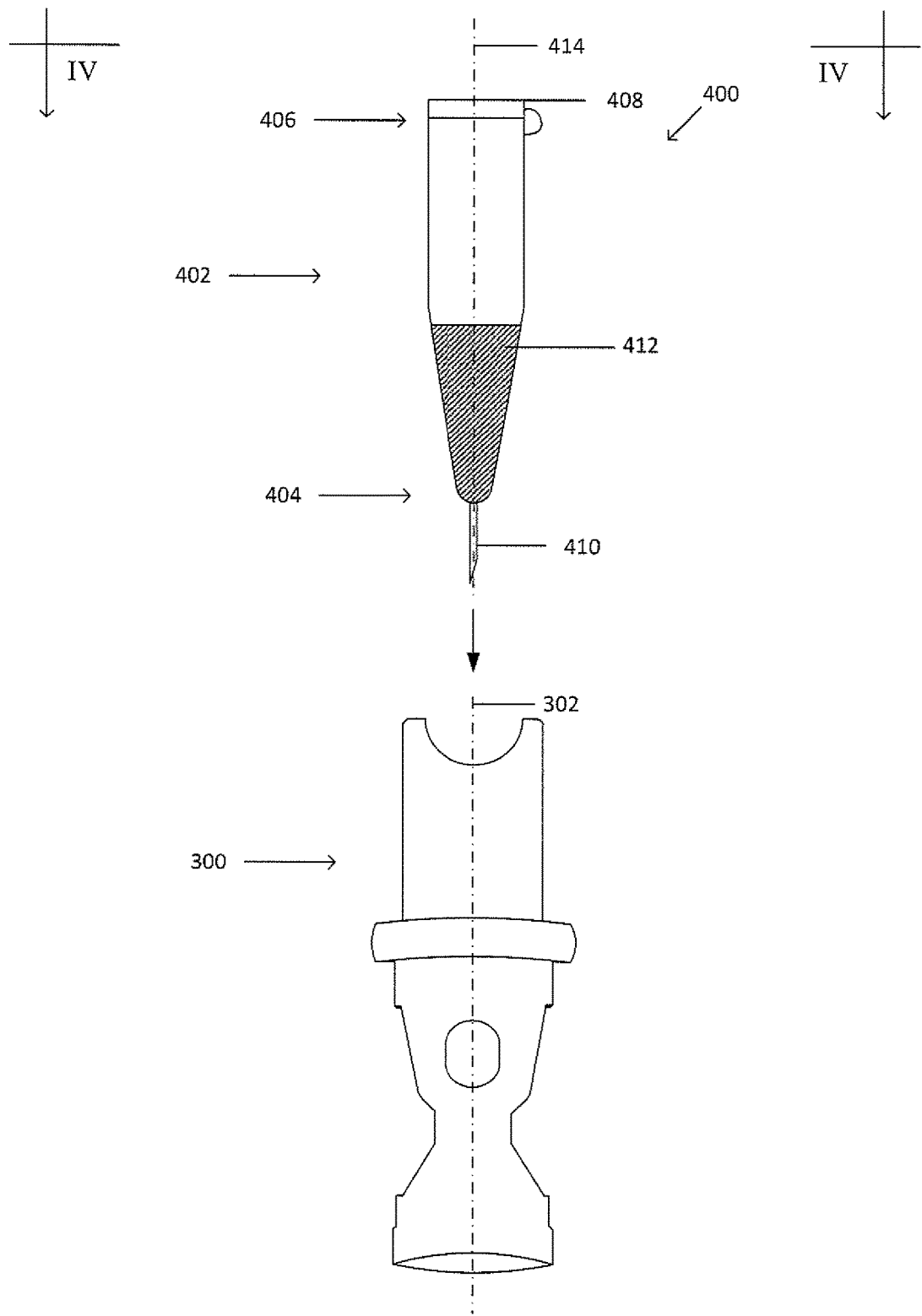

FIG. 4A shows an exploded view of the example collector 300 and a processing vessel 402. FIG. 4B shows a cross-sectional view of the processing vessel 402 inserted into the cavity 314 at the first end 306 of the collector 300 taken along the line IV-IV shown in FIG. 4A. The collector 300 and processing vessel 402 form a collector-processing vessel system 400. The processing vessel 402 may be an Eppendorf tube, a syringe, or a test tube and has a first end 406 and a second end 404. The second end 404 is sized to receive a cap 408. The cap 408 may be composed of re-sealable rubber or other suitable re-sealable material that can be repeatedly punctured with a needle or other sharp implement to access the contents stored in the processing vessel 402 interior and re-seals when the needle or implement is removed. Alternatively, the processing vessel 402 may also have two open ends that are sized to receive caps. The processing vessel 402 may have a tapered geometry that widens or narrows toward the second end 404; the processing vessel 402 may have a generally cylindrical geometry; or, the processing vessel 402 may have a generally cylindrical geometry in a first segment and a cone-shaped geometry in a second segment, where the first and second segments are connected and continuous with each other. Although at least one segment of the processing vessel 402 has a circular cross-section, in other embodiments, the at least one segment can have elliptical, square, triangular, rectangular, octagonal, or any other suitable cross-sectional shape. The processing vessel 402 can be composed of a transparent, semitransparent, opaque, or translucent material, such as plastic or another suitable material. The processing vessel includes a central axis 414, which when inserted into the cavity 314 is coaxial with the central axis 302 of the collector 300.

The processing vessel 402 includes a cannula 410 extending outwardly from the second end 404. The cannula 410 may be a tube or needle (e.g. non-coring needle) and may include a flat tip, a beveled tip, a sharpened tip, or a tapered tip. As seen in FIG. 4B, the cannula 410 has a tapered tip that punctures the septum 320 and extends into the concave opening 318. As seen in FIG. 4C, a processing vessel 422 (which is similar to the processing vessel 402) includes a cannula 424 which sits flush with the apex of the concave opening 318 and therefore does not extend into the concave opening 318.

As shown in FIGS. 4A-4C, the processing vessels 402, 422 may be loaded with a displacement fluid 412. The displacement fluid 412 is the same as the displacement fluid 122 discussed in reference to collectors 100, 200.

The processing vessel 402 may also include a processing solution (not shown) to effect a transformation on the target material when the target material enters the processing vessel 402. The processing solution (not shown) may be a preservative, a cell adhesion solution, a dye, or the like. Unlike the displacement fluid 412, most, if not all, of the processing solution (not shown) remains within the processing vessel 402 upon centrifugation, thereby effecting the transformation on the target material in one manner or another (i.e. preserving, increasing adhesion properties, or the like). The processing solution (not shown) may be introduced as a liquid or as a liquid contained in a casing. The casing may be dissolvable in an aqueous solution but not in the displacement fluid 412 (such as gel cap); or, the casing may be breakable, such that the casing breaks when the processing vessel 402 is shaken in a vortex mixer. Additionally, more than one processing solution may be used.

The processing vessel 402 may include a flexible cap that can be pushed to dispense a pre-determined volume therefrom and onto a substrate, such as a slide or a well plate. The cap 408 may be flexible or the cap 408 may be removed and the flexible cap inserted into the second end 404. Alternatively, the processing vessel 402 may be attached to (i.e. after accumulating the target material) or may include a dispenser, which is capable of dispensing a pre-determined volume of target material from the processing vessel 402 onto another substrate, such as a microscope slide. The dispenser may repeatedly puncture the re-sealable cap 408 or compress the material within the processing vessel 402 to withdraw and dispense the pre-determined volume of target material onto the substrate. Alternatively, the cap 408 may be removed and the dispenser (not shown) may be inserted directly into the processing vessel 402 to dispense the buffy coat-processing solution mixture.

The displacement fluid is inert with respect to the suspension materials. and may be miscible or immiscible in the suspension fluid or suspension components. Examples of suitable displacement fluids include, but are not limited to, solution of colloidal silica particles coated with polyvinylpyrrolidone (e.g. Percoll), polysaccharide solution (e.g. Ficoll), iodixanol (e.g. OptiPrep), an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane; and combinations thereof.

The main body of the collector may be composed of a variety of different materials including, but not limited to, a ceramic; metals; organic or inorganic materials; and plastic materials, such as polyoxymethylene ("Delrin®"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrite butadiene-styrene copolymer, butyl rubber, ethylene propylene diene monomer; and combinations thereof.

Sealing Ring

Figure 5A:
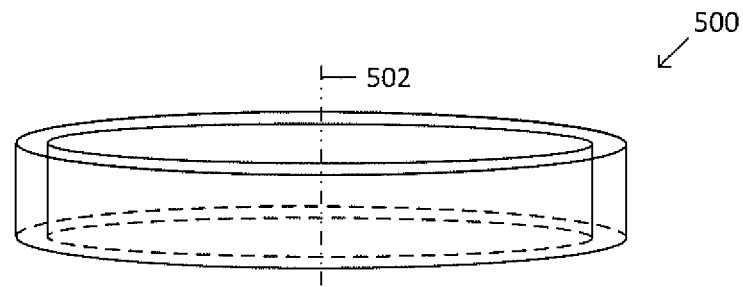
FIGS. 5A-5B show an example sealing ring.
Figure 5B:
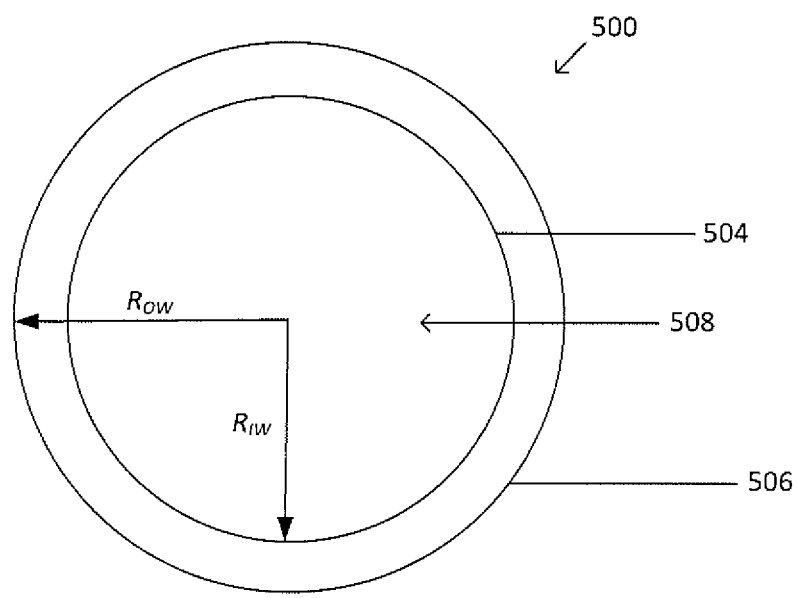

FIG. 5A shows an isometric view of a sealing ring 500. FIG. 5B shows a top down view of the sealing ring 500. Dot-dashed line 502 represents the central or highest-symmetry axis of the sealing ring 500. The sealing ring 500 includes an inner wall 504, an outer wall 506, and a cavity 508. In FIG. 4B, $R_{IW}$ represents the radial distance from the center of the sealing ring 500 to the inner wall 504, and $R_{OW}$ represents the radial distance from the center of the sealing ring 500 to the outer wall 506. The sealing ring 500 is configured to fit around a vessel, such as a tube. The cavity 508 is sized and shaped to receive the vessel. The sealing ring 500 may be tightened, such that the size of the cavity 508 and the radii of the inner and outer walls 504 and 506 are reduced by circumferentially applying an approximately uniform, radial force, such as the radial force created by a clamp, around the outer wall 506 directed to the central axis 502 of the sealing ring 500. When the sealing ring 500 is tightened around the vessel, the uniform force applied to the sealing ring 500 is applied to the vessel, thereby causing the vessel to constrict. When the radial force is removed from the sealing ring 500, the sealing ring 500 remains tightened and in tension around the vessel, thereby causing the vessel to remain in the constricted state.

Figure 5C:
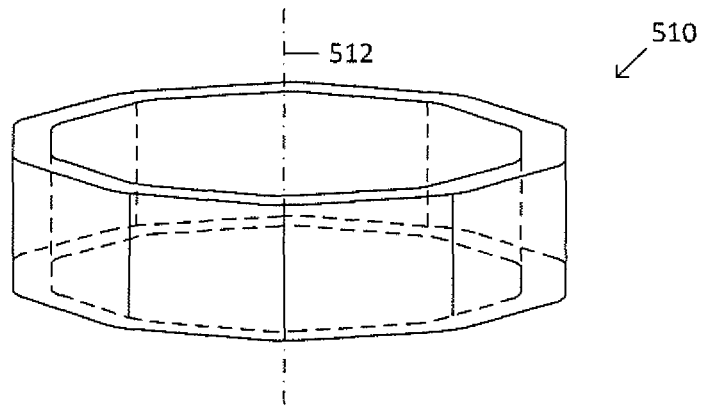
FIG. 5C-5D show an example sealing ring.
Figure 5D:
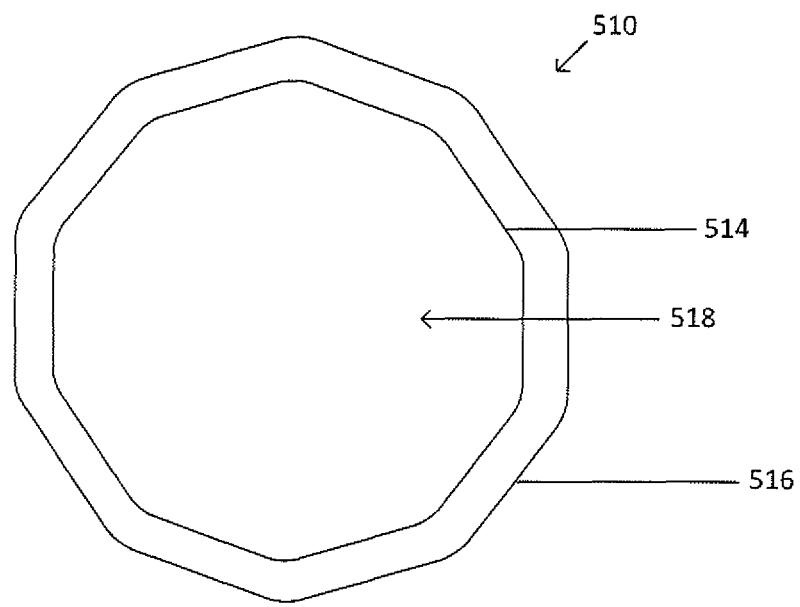

The sealing ring may be any shape, including, but not limited to, circular, triangular, or polyhedral. FIG. 5C shows an isometric view of a sealing ring 510. FIG. 5D shows a top down view of the sealing ring 510. Sealing ring 510 is similar to sealing ring 500, except sealing ring 510 is polyhedral. Dot-dashed line 512 represents the central or highest-symmetry axis of the sealing ring 510. The sealing ring 510 includes an inner wall 514, an outer wall 516, and a cavity 518. The sealing ring may be composed of a metal, such as brass, a polymer, or combinations thereof.

Figure 5E:
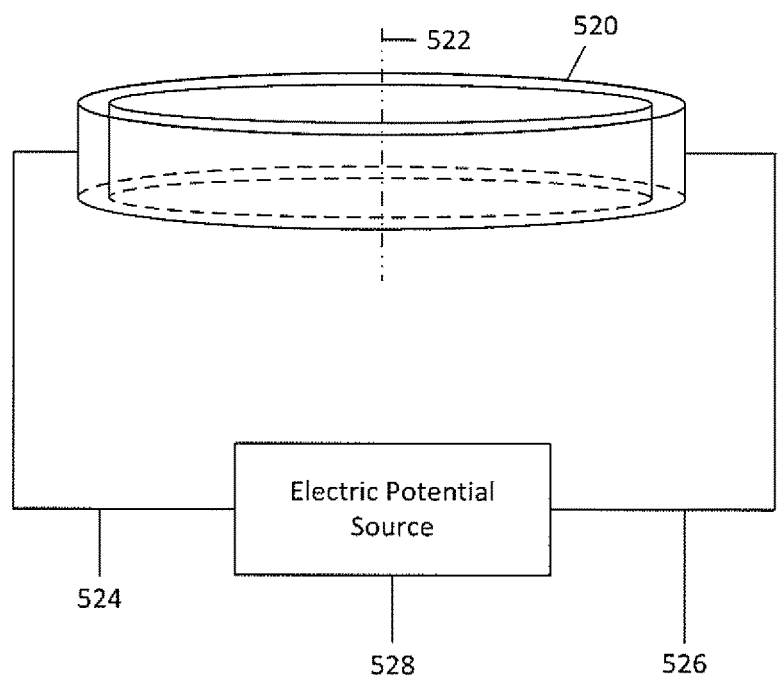
FIGS. 5E-5F show an example sealing ring.
Figure 5F:
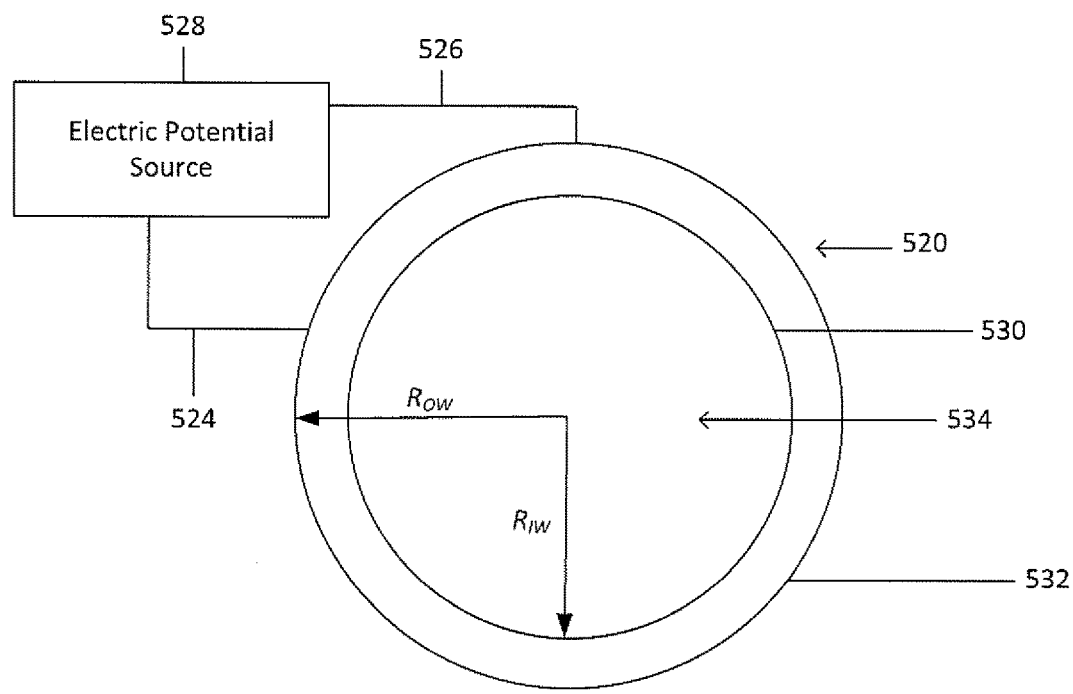

Alternatively, as shown in FIG. 5E, a sealing ring 520 may be composed of a piezoelectric material. Dot-dashed line 522 represents the central or highest-symmetry axis of the sealing ring 520. The sealing ring 520 may be connected to an electric potential source 528, such as a battery, via a first lead 524 and a second lead 526. The electric potential source 528 creates an electric potential that when applied to the sealing ring 520 produces a mechanical strain that causes the sealing ring 520 to tighten (i.e. sealing ring 520 tightens when an electric potential is applied). FIG. 4F shows a top down view of the sealing ring 520. The sealing ring 520 includes an inner wall 550, an outer wall 552, and a cavity 554. In FIG. 4F, $R_{IW}$ represents the radial distance from the center of the sealing ring 520 to the inner wall 550, and $R_{OW}$ represents the radial distance from the center of the sealing ring 520 to the outer wall 552. When the sealing ring 520 is composed on the piezoelectric material, a clamp is not required, because the mechanical strain causes the sealing ring 520 to tighten without applying an external force, except for the requisite electric potential. Alternatively, the sealing ring 520 may be in a naturally tightened stated. When applying the electric potential the sealing ring 520 expands. Alternatively, a portion of the sealing ring may be composed of the piezoelectric material, such that the piezoelectric portion acts as an actuator to cause the other portion of the sealing ring to tighten and apply the substantially uniform circumferential pressure on the tube, thereby constricting the tube to form the seal.

Figure 5G:
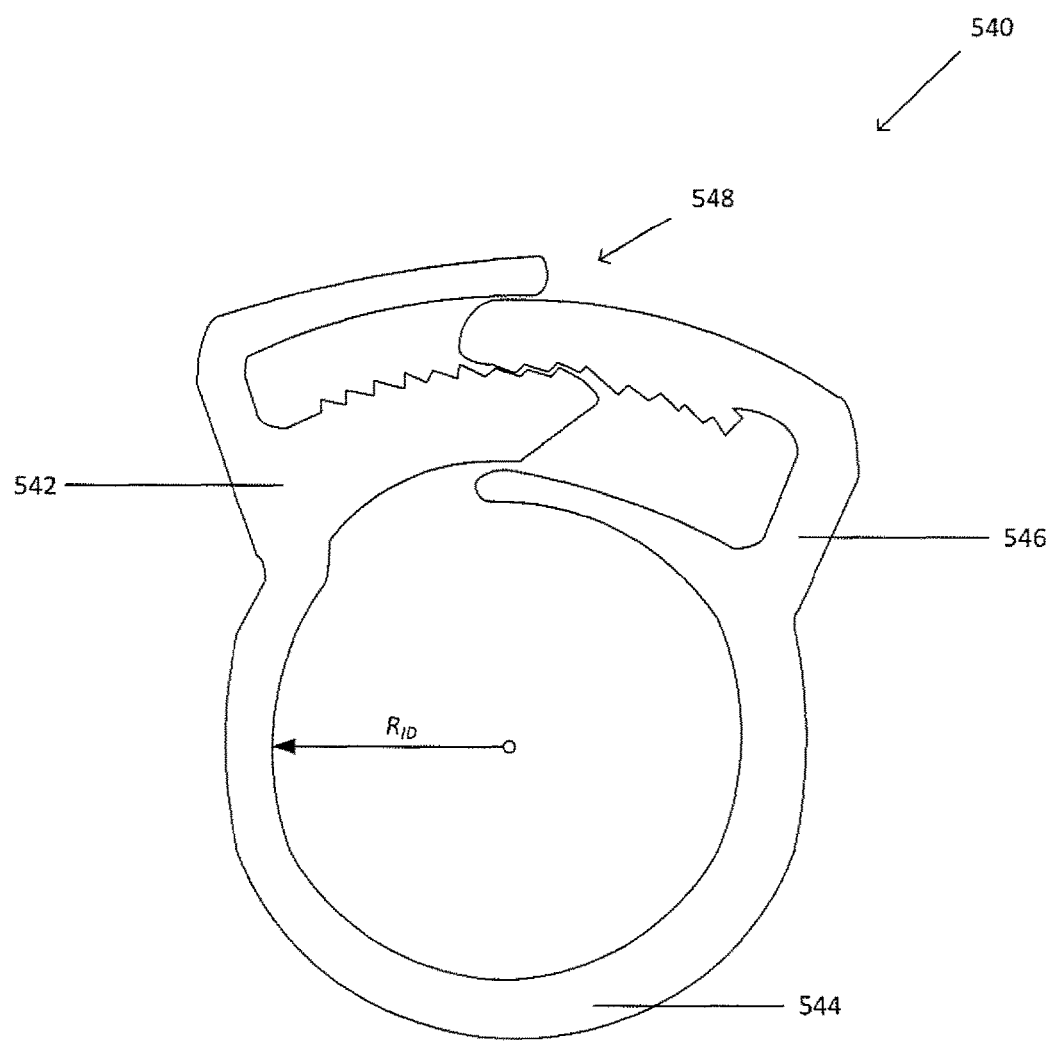
FIG. 5G shows an example sealing ring.

FIG. 5G shows an isometric view of a sealing ring 540. The sealing ring includes an adjustment mechanism 548 to adjust the inner diameter $R_{ID}$. The collapsible ring includes a first end 542 and a second end 546, the first and second ends 542 and 546 being joined by a band portion 544. The first and second ends 542 and 546 include complementary portions of the adjustment mechanism 548. The adjustment mechanism 548 includes, but is not limited to, a ratchet, tongue and groove, detents, or the like.

The sealing ring may also include a thermal element, such as a heated wire. The thermal element may soften the vessel for constriction. Alternatively, the thermal element may melt the vessel to provide a more adherent seal. Alternatively, the thermal element may cause the sealing ring to compress, thereby forming a seal between the tube and float.

Method

For the sake of convenience, the methods are described with reference to an example suspension of anticoagulated whole blood. But the methods described below are not intended to be so limited in their scope of application. The methods, in practice, can be used with any kind of suspension. For example, a sample suspension can be urine, blood, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. It should also be understood that a target material can be a fraction of a sample suspension, such as Buffy coat, a cell, such as ova, a fetal cell, a fetal nucleated red blood cell, or a circulating tumor cell ("CTC"), a circulating endothelial cell, a fetal cell, a vesicle, a liposome, a protein, a nucleic acid, a biological molecule, a naturally occurring or artificially prepared microscopic unit having an enclosed membrane, parasites, microorganisms, viruses, or inflammatory cells.

Figure 6:
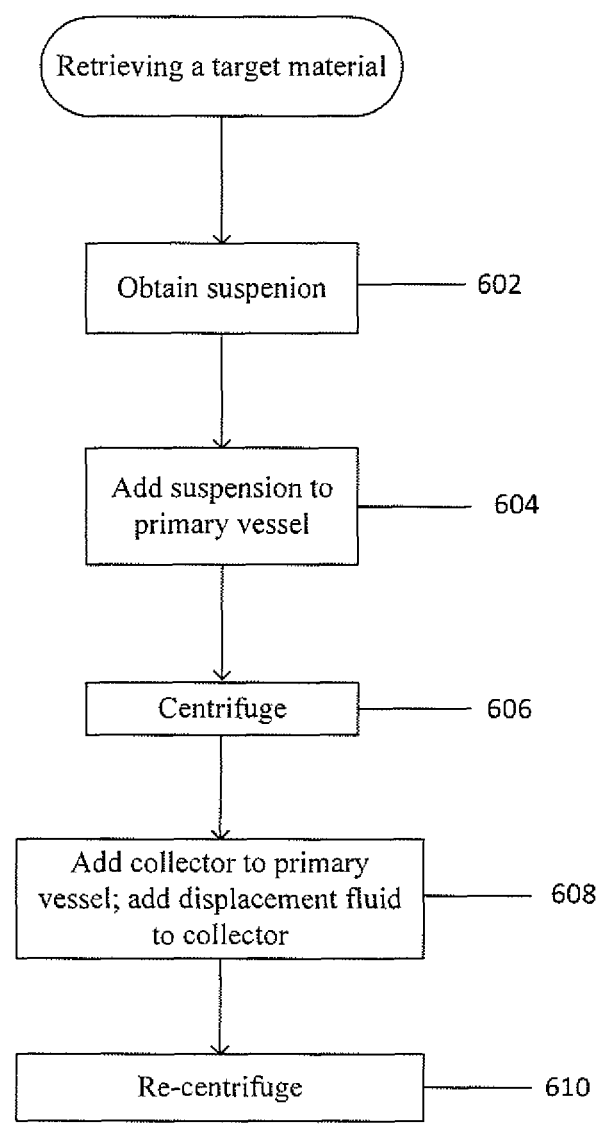
FIG. 6 shows a flow diagram of an example method for retrieving a target material.

FIG. 6 shows a flow diagram for an example method for retrieving a target material. In block 602, a suspension, such as anticoagulated whole blood, is obtained. In block 604, the whole blood is added to a primary vessel, such as a test tube. A float may also be added to the primary vessel. For the sake of convenience, the methods are described with reference to the float, but the methods described below are not intended to be so limited in their application and may be performed without the float.

FIG. 7A shows an isometric view of an example primary vessel and float system 700. The system 700 includes a primary vessel 702 and a float 704 suspended within whole blood 706. In the example of FIG. 7A, the primary vessel 702 has a circular cross-section, a first closed end 710, and a second open end 708. The open end 708 is sized to receive a cap 712. The primary vessel may also have two open ends that are sized to receive caps, such as the example tube and separable float system 720 shown FIG. 7B. The system 720 is similar to the system 700 except the primary vessel 702 is replaced by a primary vessel 722 that includes two open ends 724 and 726 configured to receive the cap 712 and a cap 728, respectively. The primary vessels 702 and 722 have a generally cylindrical geometry, but may also have a tapered geometry that widens, narrows, or a combination thereof toward the open ends 710 and 724, respectively. Although the primary vessels 702 and 722 have a circular cross-section, in other embodiments, the primary vessels 702 and 722 can have elliptical, square, triangular, rectangular, octagonal, or any other suitable cross-sectional shape that substantially extends the length of the tube. The primary vessels 702 and 722 can be composed of a transparent, semitransparent, opaque, or translucent material, such as plastic or another suitable material. The primary vessels 702 and 722 each include a central axis 718 and 730, respectively. The primary vessel 702 may also include a plug 714, as seen in magnified view 716, at the closed end 708 to permit the removal of a fluid, the suspension, or a suspension fraction, whether with a syringe, a pump, by draining, or the like. The primary vessel 702 may have a sidewall and a first diameter.

The plug 714 may be composed of re-sealable rubber or other suitable re-sealable material that can be repeatedly punctured with a needle or other sharp implement to access the contents of the primary vessel 702 interior and re-seals when the needle or implement is removed. The plug 714 can be formed in the openings and/or the bottom interior of the tube using heated liquid rubber that can be shaped and hardens as the rubber cools. The adhesive used to attach the plug 714 to the wall of the opening and tube interior and can be a polymer-based adhesive, an epoxy, a contact adhesive or any other suitable material for bonding rubber to plastic or creating a thermal bond.

FIGS. 7A-7B show the float 704. The float 704 includes a main body, two teardrop-shaped end caps, and support members radially spaced and axially oriented on the main body. The float 704 can also include two dome-shaped end caps or two cone-shaped end caps or any appropriately-shaped end cap. The support members may engage the inner wall of the primary vessel 702. Alternatively, the float 704 may not include any support members. Alternatively, the float 704 may include support members which do not engage the inner wall of the primary vessel 702.

In alternative embodiments, the number of support members, support member spacing, and support member thickness can each be independently varied. The support members can also be broken or segmented. The main body is sized to have an outer diameter that is less than the inner diameter of the primary vessel 702, thereby defining fluid retention channels between the outer surface of the main body and the inner wall of the primary vessel 702. The surfaces of the main body between the support members can be flat, curved or have another suitable geometry. The support members and the main body may be a singular structure or may be separate structures.

Embodiments include other types of geometric shapes for float end caps. The top end cap may be teardrop-shaped, dome-shaped, cone-shaped, or any other appropriate shape. The bottom end cap may be teardrop-shaped, dome-shaped, cone-shaped, or any other appropriate shape. In other embodiments, the main body of the float 704 can include a variety of different support structures for separating samples, supporting the tube wall, or directing the suspension fluid around the float during centrifugation. Embodiments are not intended to be limited to these examples. The main body may include a number of protrusions that provide support for the tube. In alternative embodiments, the number and pattern of protrusions can be varied. The main body may include a single continuous helical structure or shoulder that spirals around the main body creating a helical channel. In other embodiments, the helical shoulder can be rounded or broken or segmented to allow fluid to flow between adjacent turns of the helical shoulder. In various embodiments, the helical shoulder spacing and rib thickness can be independently varied. In another embodiment, the main body may include a support member extending radially from and circumferentially around the main body. In another embodiment, the support members may be tapered.

The float 704 can be composed of a variety of different materials including, but not limited to, metals; organic or inorganic materials; ferrous plastics; sintered metal; machined metal; plastic materials and combinations thereof. The primary vessel 702 may have a sidewall and a first diameter. The float 704 can be captured within the primary vessel 702 by an interference fit, such that under centrifugation, a sidewall of the tube expands to permit axial movement of the float 704. When centrifugation stops, the sidewall reduces back to the first diameter to induce the interference fit. Alternatively, the sidewall may not expand and the interference fit may not occur between the float 704 and the primary vessel 702, such that the float moves freely within the tube before, during, or after centrifugation.

The cap may be composed of a variety of different materials including, but not limited to, organic or inorganic materials; plastic materials; and combination thereof.

The end caps of the float may be manufactured as a portion of the main body, thereby being one singular structure, by machining, injection molding, additive techniques, or the like; or, the end caps may be connected to the main body by a press fit, an adhesive, a screw, any other appropriate method by which to hold at least two pieces together, or combinations thereof.

Figure 8:
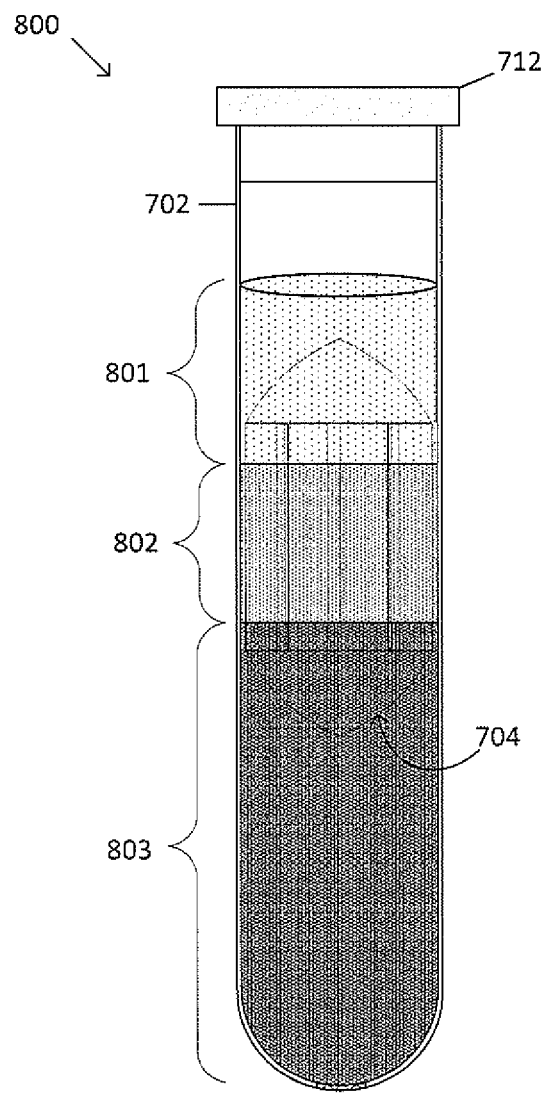
FIG. 8 shows an example float and primary vessel system having undergone density-based separation.

Returning to FIG. 6, in block 606, the primary vessel, the float, and the whole blood undergo density-based separation, such as by centrifugation, thereby permitting separation of the whole blood into density-based fractions along an axial position in the tube based on density. FIG. 8 shows an isometric view of the primary vessel and float system 700 having undergone density-based separation, such as by centrifugation. Suppose, for example, the whole blood includes three fractions. For convenience sake, the three fractions include plasma, buffy coat, and red blood cells. However, when another suspension undergoes centrifugation, there may be more than, less than, or the same number of fractions, each fraction having a different density. The suspension separates into three fractions along an axial position in the tube based on density, with red blood cells 803 located on the bottom, plasma 801 located on top, and buffy coat 802 located in between. The float 704 may have any appropriate density to settle within one of the fractions. The density of the float 704 can be selected so that the float 704 settles at the same axial position of the buffy coat 802. The buffy coat 802 can be trapped within an area between the float 704 and the primary vessel 702.

At least one delineation fluid (not shown) may be used to provide further separation between the target material and any non-target material above and/or below the target material. For example, to further separate the buffy coat 802 and the plasma 801 and the buffy coat 802 and the red blood cells 803. The at least one delineation fluid (not shown) may have a density greater than or less than the target material. For example, when it is desirous to further separate the buffy coat 802 and the red blood cells 803, the delineation fluid may have a density greater than the buffy coat 802 and less than the red blood cells 803. The at least one delineation fluid (not shown) may be miscible or immiscible with the suspension fluid and inert with respect to the suspension materials. The density of the at least one delineation fluid (not shown) may be static (e.g. remaining constant) or dynamic (e.g. changing based on outside or environmental conditions, including pressure or temperature). The at least one delineation fluid (not shown) may also provide an area in which to seal the primary vessel 702, as there is greater delineation and separation between the buffy coat 802 and the red blood cells 803. The at least one delineation fluid (not shown) may be used whether or not a float is used. Examples of suitable delineation fluids include, but are not limited to, solution of colloidal silica particles coated with polyvinylpyrrolidone (e.g. Percoll), polysaccharide solution (e.g. Ficoll), iodixanol, cesium chloride, sucrose, sugar-based solutions, polymer-based solutions, surfactants, an organic solvent, a liquid wax, an oil, a gas, and combinations thereof; olive oil, mineral oil, silicone oil, chill-out liquid wax, paraffin wax, microcrystalline waxes, soy and palm waxes, candle waxes, thermoset waxes, hot melt adhesives, atactic polypropylene and polyolefin compounds, petroleum waxes, dental waxes, animal waxes, vegetable waxes, mineral waxes, petroleum waxes, and synthetic waxes, such as ethylenic polymers, chlorinated naphthalenes or hydrocarbon-type waxes; immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane.

Figure 9B:
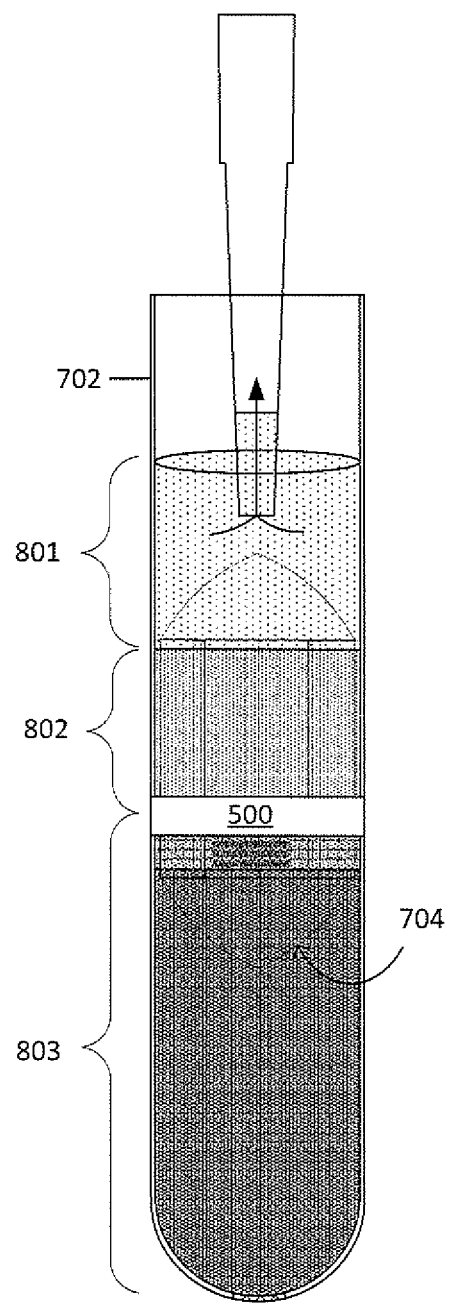

FIG. 9A shows a seal being formed to prevent fluids from moving up or down within the primary vessel. The seal also inhibits float movement. The sealing ring 500 exerts circumferential or radial forces on the primary vessel 702, thereby causing the primary vessel 702 to collapse inwardly against the float 704. Magnified view 902 shows the sealing ring 500 tightened around the float and primary vessel system 700. The sealing ring 500, having been placed at an interface of the buffy coat 802 and the red blood cells 803, causes the primary vessel 702 to collapse inwardly until a seal is formed between the primary vessel 702 and the float 704. An outer wall of the sealing ring 500 may sit flush with an outer wall of the primary vessel 702; the outer wall of the sealing ring 500 may extend past the outer wall of the primary vessel 702; or, the outer wall of the primary vessel 702 may extend past the outer wall of the sealing ring 500. The sealing ring 500 remains tightened to maintain the seal, which prevents fluids from moving past the seal in any direction. The sealing ring 500 may also remain in tension. Alternatively, the sealing ring 500 may be overtightened and then the force applied to the sealing ring 500 is removed. The sealing ring 500 may expand slightly, though still remains constricted.

To apply the sealing ring 500 and thereby form the seal, a clamp may be used to circumferentially apply a force directed toward the central axis of the primary vessel 702 to the sealing ring 500 and the float and primary vessel system 700. The sealing ring 500 is placed around the float and primary vessel system 700 after the float and primary vessel system 700 have undergone density-based separation, such as by centrifugation. The sealing ring 500 and float and primary vessel system 700 are then placed into the clamp. The clamp may include a shelf to support the sealing ring 500 against the primary vessel 702. Operation of the clamp may be automated or may be performed manually. Alternatively, the clamp may form a seal between the float 704 and primary vessel 702 without the inclusion of the sealing ring 500. Alternatively, a seal may be formed between the float 704 and the primary vessel 702 such as by ultrasonic welding; or by applying heat or a temperature gradient to deform and/or melt the primary vessel 702 to the float 704. For the sake of convenience, the methods are described with reference to the seal between the float and the primary vessel, but the methods described below are not intended to be so limited in their application and may be performed without the seal.

When operation of the clamp is automated, a motor causes translation of either a collet, including collet fingers, or a pressure member to cause compression of the collet fingers. The motor may be connected to the collet or the pressure member by a shaft, such as a cam shaft, and one or more gears. A base engages and holds the object. When the collet is driven by the motor, the pressure member remains stationary. When the pressure member is driven by the motor, the collet remains stationary. The clamp may include a release, so as to cause the pressure member to slide off of the collet fingers, thereby removing the clamping force.

Alternatively, the clamp may be, but is not limited to, a collet clamp, an O-ring, a pipe clamp, a hose clamp, a spring clamp, a strap clamp, or a tie, such as a zip tie. The clamp may be used without a sealing ring to provide a seal between a float and a tube.

Figure 9E:
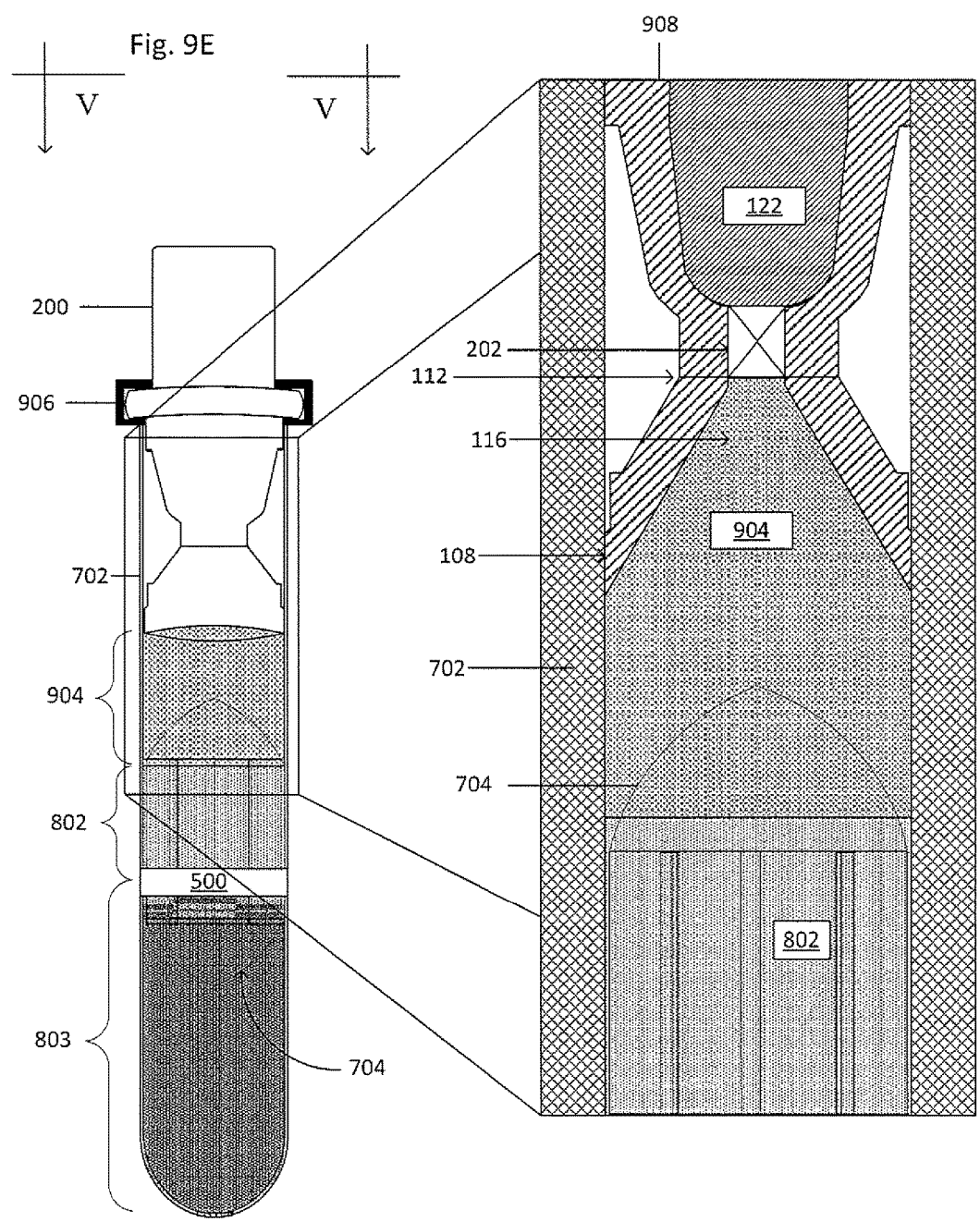
Figure 10A:
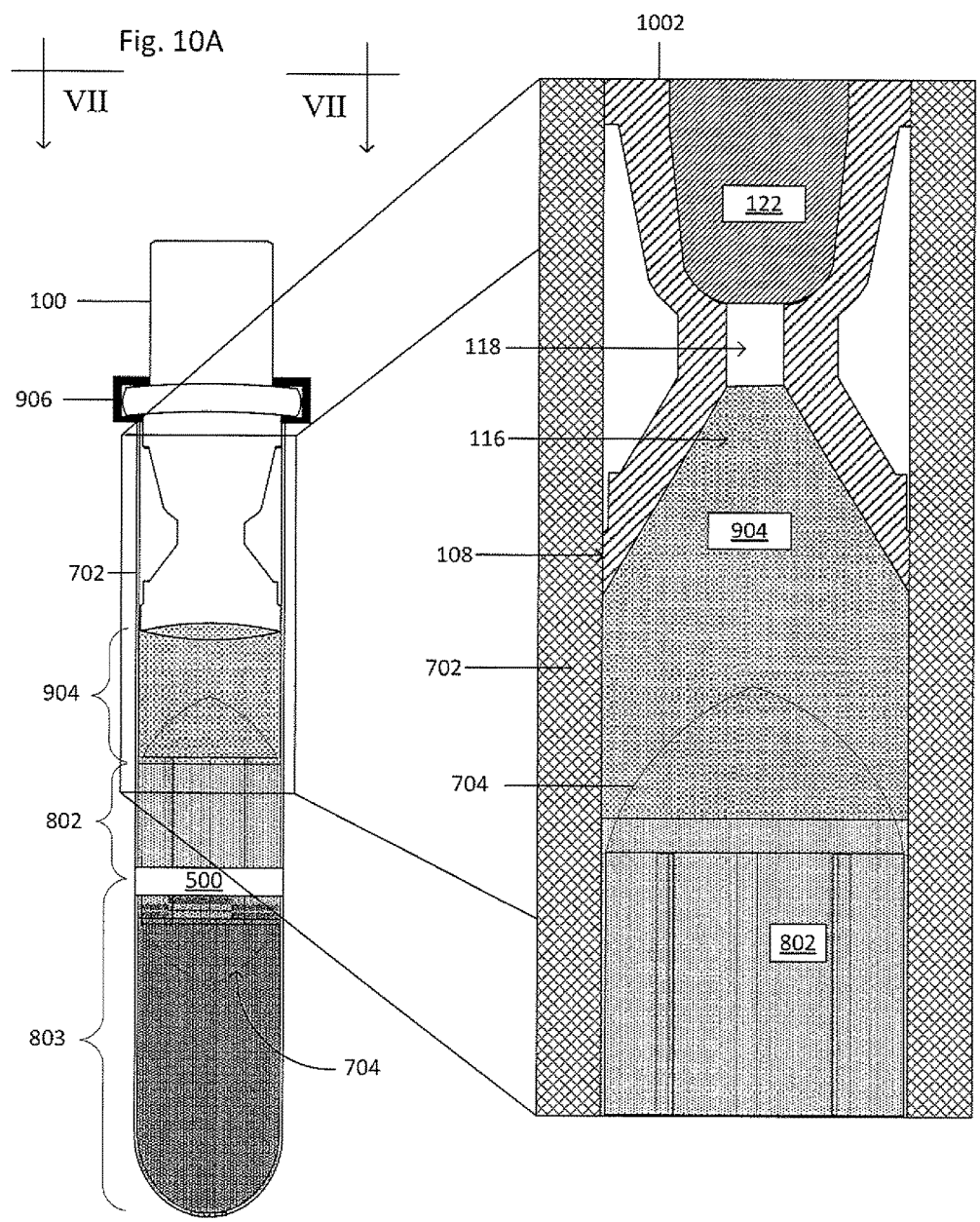
Figure 11A:
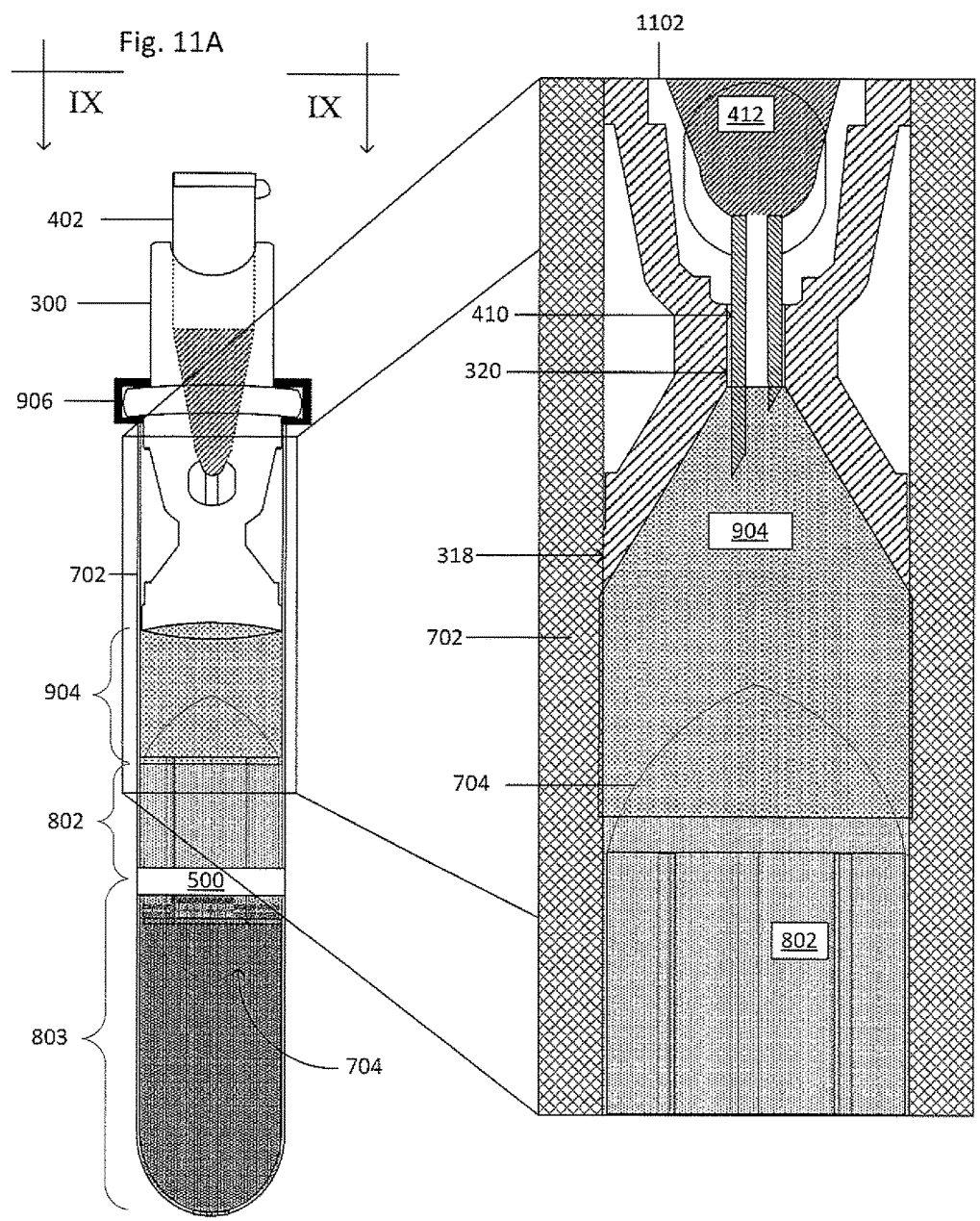

The plasma 801 may be removed from the primary vessel 702, as seen in FIG. 8B, such as by pipetting, suctioning, pouring, or the like. Returning to FIG. 6, in block 608, a collector is inserted into a primary vessel and a displacement fluid is added to the collector. The displacement fluid may be added to the collector before or after the collector is inserted into the primary vessel. A clearing fluid may also be added to the primary vessel before the collector is inserted. FIGS. 8C-8D show a clearing fluid 904 having a density greater than at least the buffy coat 802 (i.e. may have a density greater than the buffy coat but less than the red blood cells, or may have a density greater than both the buffy coat and the red blood cells, for example) being added to the primary vessel 702. The collector 200 is then added to the primary vessel 702, as seen in FIG. 9E. Alternatively, the collector 100 is then added to the primary vessel 702, as seen in FIG. 10A. Alternatively, the collector-processing vessel system 400 including the collector 300 and the processing vessel 402 is then added to the primary vessel 702, as seen in FIG. 11A.

The displacement fluid 122 may be added to the collector 200 before or after the collector 200 is inserted into the primary vessel 702. The second end 208 of the collector 200 may form an interference fit with the sidewall of the primary vessel 702 to prevent fluid from flowing around the collector 200 before, during, and after centrifugation. A lock ring 906 may be placed over the shoulder 110 of the collector 200 and the open end 710 of the primary vessel 702 to inhibit translation of the collector 200 relative to the primary vessel 702. Magnified view 908, which is a cross-section taken along the line V-V, shows the displacement fluid 122 in the collector 222 and the clearing fluid 904 and the buffy coat 802 in the primary vessel 702. Alternatively, magnified view 1002, which is a cross-section taken along the line VII-VII, shows the displacement fluid 122 in the collector 100 and the clearing fluid 904 and the buffy coat 802 in the primary vessel 702. Alternatively, magnified view 1102, which is a cross-section taken along the line IX-IX, shows the displacement fluid 412 in the processing vessel 402 and the clearing fluid 904 and the buffy coat 802 in the primary vessel 702.

The clearing fluid has a greater density than the density of at least material above the sealing ring when the sealing ring is compressed against the float or at least the target material when no float or sealing ring are used. The clearing fluid is inert with respect to the suspension materials and may be miscible or immiscible in the suspension fluid. Examples of suitable clearing fluids include, but are not limited to, solution of colloidal silica particles coated with polyvinylpyrrolidone (e.g. Percoll), polysaccharide solution (e.g. Ficoll), iodixanol (e.g. OptiPrep), an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydro fluoro carbons, perfluorocarbons, perfluoropolyethers, silicon and silicon-based liquids, such as phenylmethyl siloxane; and combinations thereof.

Figure 9F:
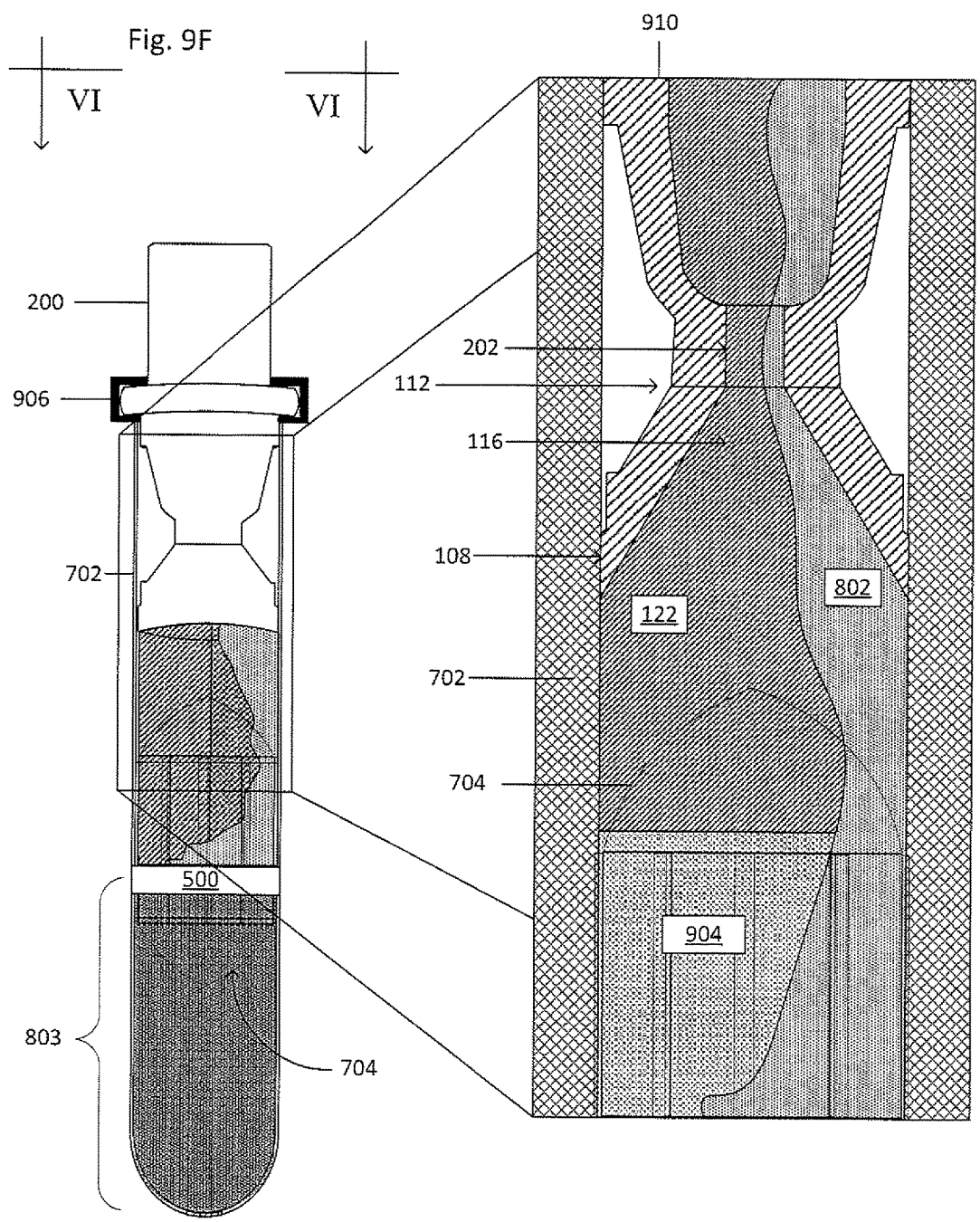
Figure 9G:
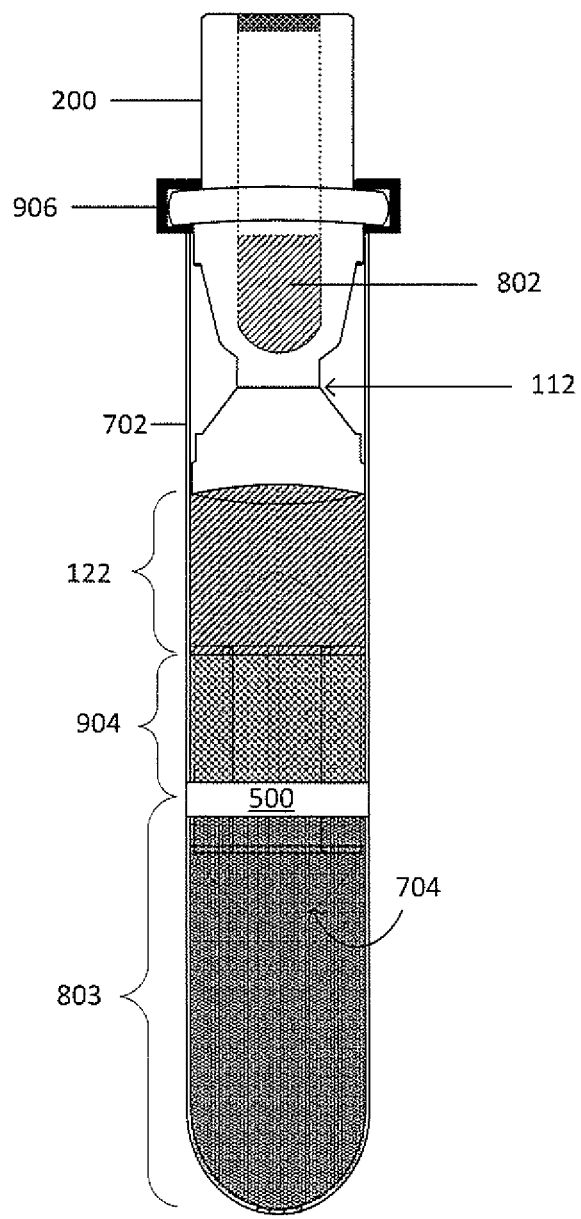

Returning to FIG. 6, in block 610, the system is then re-centrifuged. FIG. 9F shows the collector 200 and the primary vessel 702 undergoing centrifugation. Magnified view 910, which is a cross-section view taken along the line VI-VI, shows the exchange of fluids between the primary vessel 702 and the collector 200. During centrifugation, the valve 206 opens to permit fluid to flow into and out of the collector 200. As the clearing fluid 904, having a greater density than the buffy coat 802, moves down in the primary vessel 702, the buffy coat 802 is cleared from the float 704. As the displacement fluid 122, having a density greater than the buffy coat 802 but less than the clearing fluid 904, flows from the collector 200 into the primary vessel 702, the buffy coat 802 moves upwards within the primary vessel 702, into the second end 208 of the collector 200, through the valve 206, and into the cavity 214. As seen in FIG. 9G, the buffy coat 802 may then be found in the cavity 214 of the collector 200, while the displacement fluid 122 and the clearing fluid 704 are found in the primary vessel 702.

Figure 10C:
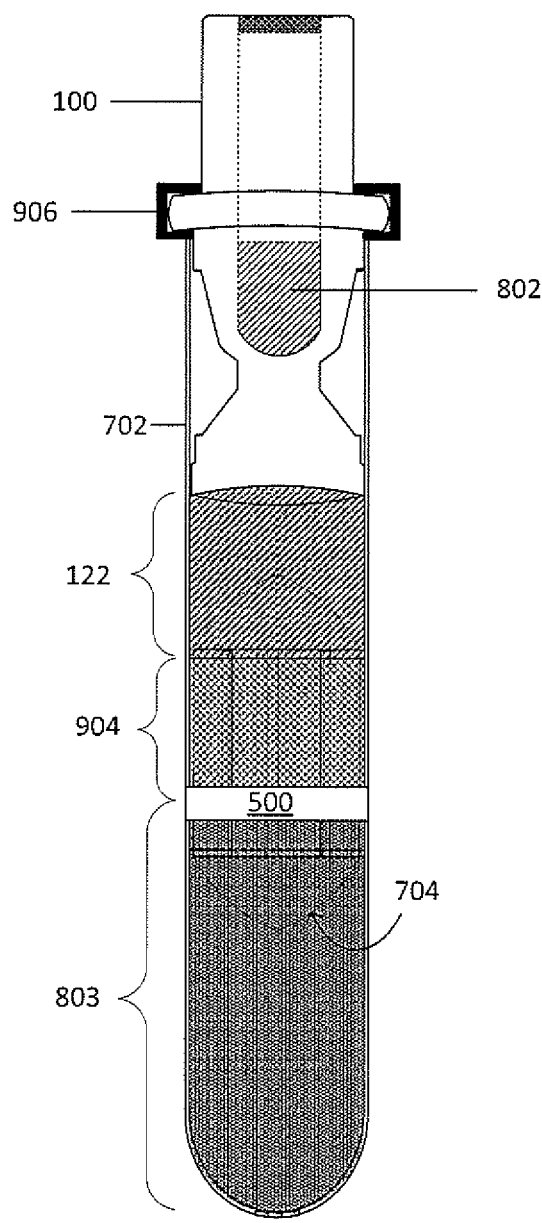

Alternatively, FIG. 10B shows the collector 100 and the primary vessel 702 undergoing centrifugation. Magnified view 1004, which is a cross-section view taken along the line VIII-VIII, shows the exchange of fluids between the primary vessel 702 and the collector 100. During centrifugation, the force, due to centrifugation, permits fluid to flow into and out of the collector 120 via the inner bore 134. As the clearing fluid 904, having a greater density than the buffy coat 802, moves down in the primary vessel 702, the buffy coat 802 is cleared from the float 704. As the displacement fluid 122, having a density greater than the buffy coat 802 but less than the clearing fluid 904, flows from the collector 120 into the primary vessel 702, the buffy coat 802 moves upwards within the primary vessel 702, into the second end 128 of the collector 120, through the inner bore 134, and into the cavity 132. As seen in FIG. 10C, the buffy coat 802 may then be found in the cavity 132 of the collector 120, while the displacement fluid 122 and the clearing fluid 904 are found in the primary vessel 702.

Figure 11C:
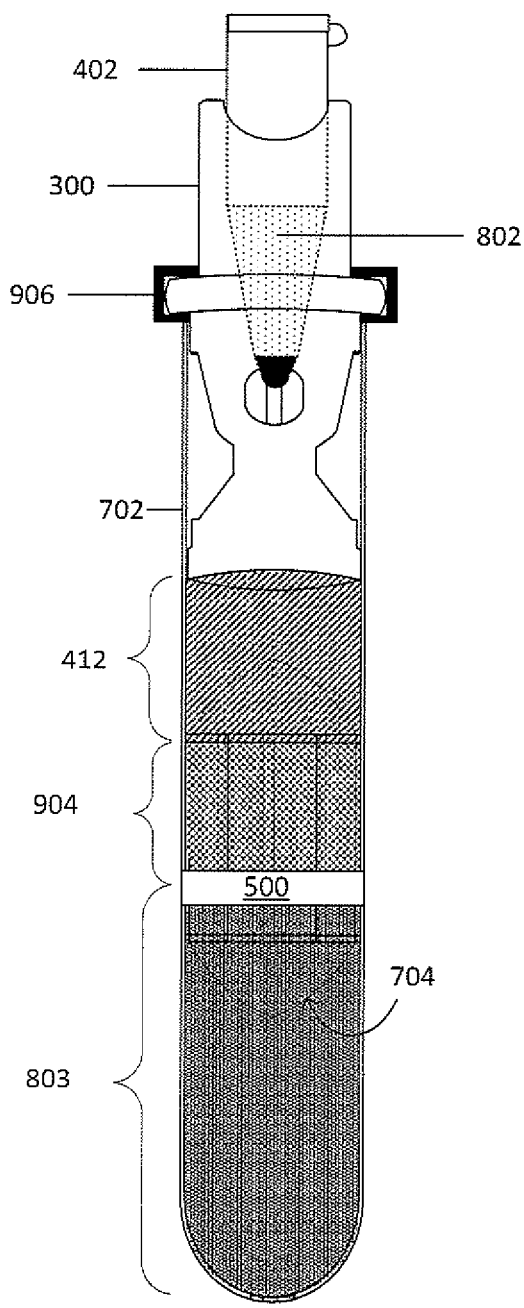

Alternatively, FIG. 11B shows the collector-processing vessel system 400 and the primary vessel 702 undergoing centrifugation. Magnified view 1104, which is a cross-section view taken along the line X-X, shows the exchange of fluids between the primary vessel 702 and the processing vessel 402 via the collector 300. During centrifugation, the clearing fluid 904, having a greater density than the buffy coat 802, moves down in the primary vessel 702, the buffy coat 802 is cleared from the float 704. As the displacement fluid 412, having a density greater than the buffy coat 802 but less than the clearing fluid 904, flows from the processing vessel 402 via the collector 320 into the primary vessel 702, the buffy coat 802 moves upwards within the primary vessel 702, into the second end 318 of the collector 300, through the cannula 410, and into the processing vessel 402. As seen in FIG. 11C, the buffy coat 802 may then be found in the processing vessel 402, while the displacement fluid 140 and the clearing fluid 904 are found in the primary vessel 702.

Figure 9H:
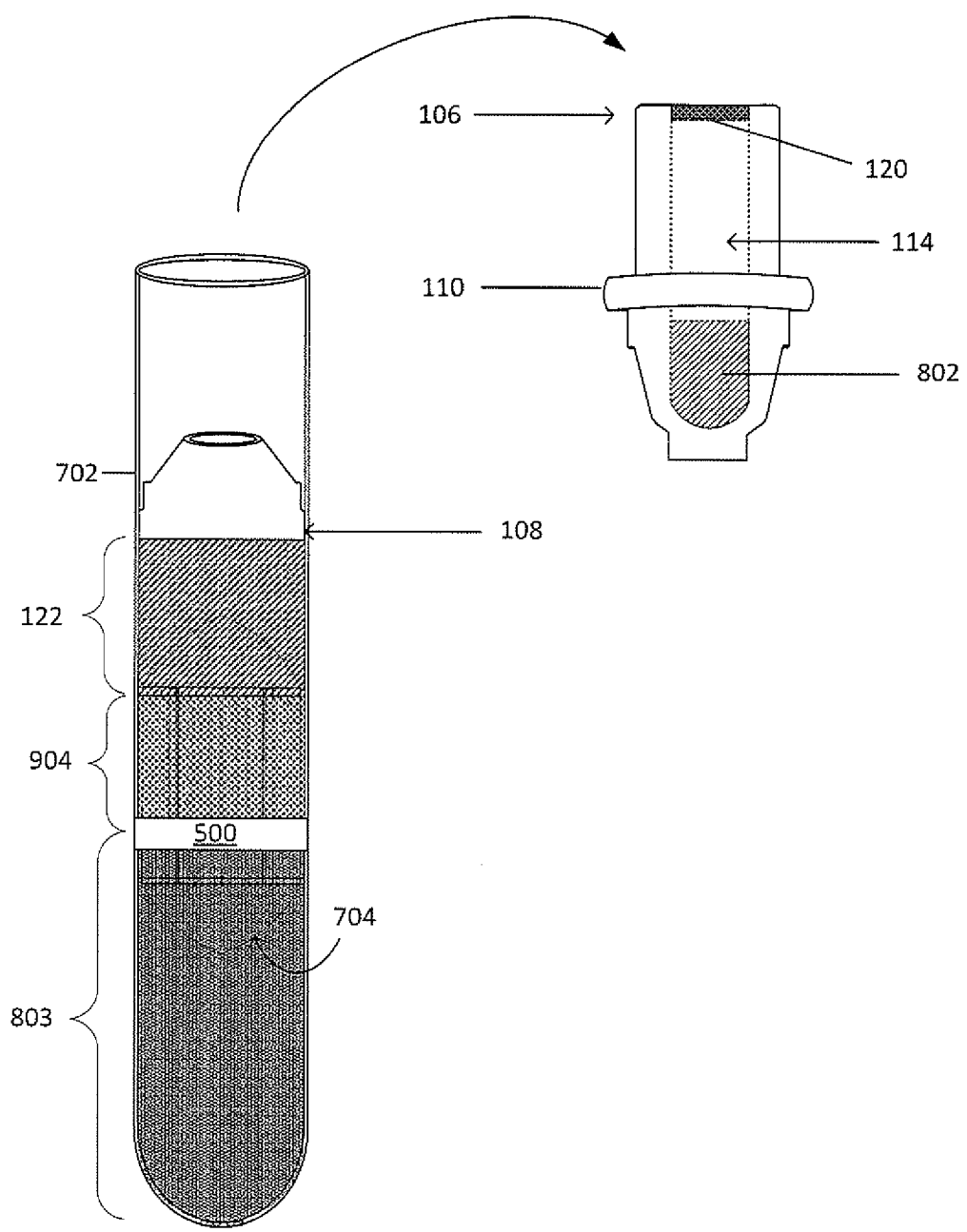

The buffy coat 802 may then be removed from the collector 200, such as by pipetting, pouring off, suctioning, or the like, and undergo further processing, analysis, storage, or the like. Alternatively, the portion of the main body 204 and the first end 206 may be removed from the primary vessel 702 by detaching or separating that portion of the main body 204 from the portion of the main body 204 that includes the concave opening 220 and the second end 208 at the break-point 212, as seen in FIG. 9H. The collector 100 may also include a plug (not shown) to seal an open end of the inner bore 118 to prevent the target material 802 from leaking out. Alternatively, the processing vessel 402 may be removed from the collector 320.

A processing solution may be added to the buffy coat 802. The processing solution (not shown), such as in liquid form, in a dissolvable casing, or in a breakable casing, may then mix with the buffy coat to effect a transformation and form a buffy coat-processing solution mixture. The buffy coat-processing solution mixture may then be dispensed onto a substrate, such as a microscope slide.

Alternatively, more than one displacement fluid may be used. Consecutive fractions may be removed from the primary vessel by displacing the respective fractions with the respective displacement fluids. For example, a first processing vessel may include a first displacement fluid to displace the plasma into the first processing vessel. A second processing vessel may include a second displacement fluid to displace the buffy coat into the second processing vessel; the second processing vessel may also include the processing solution to effect a change on the buffy coat.

The target material may be analyzed using any appropriate analysis method or technique, though more specifically extracellular and intracellular analysis including intracellular protein labeling; chromogenic staining; nucleic acid analysis, including, but not limited to, DNA arrays, expression arrays, protein arrays, and DNA hybridization arrays; in situ hybridization ("ISH"—a tool for analyzing DNA and/or RNA, such as gene copy number changes); polymerase chain reaction ("PCR"); reverse transcription PCR; or branched DNA ("bDNA"—a tool for analyzing DNA and/or RNA, such as mRNA expression levels) analysis. These techniques may require fixation, permeabilization, and isolation of the target material prior to analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Akt1, Akt2, c-myc, caspases, survivin, $p27^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist1, Snail1, ZEB1, Fibronectin, Slug, Ki-67, M30, MAGEA3, phosphorylated receptor kinases, modified histones, chromatin-associated proteins, and MAGE. To fix, permeabilize, or label, fixing agents (such as formaldehyde, formalin, methanol, acetone, paraformaldehyde, or glutaraldehyde), detergents (such as saponin, polyoxyethylene, digitonin, octyl β-glucoside, octyl β-thioglucoside, 1-S-octyl-β-D-thioglucopyranoside, polysorbate-20, CHAPS, CHAPSO, (1,1,3,3-Tetramethylbutyl)phenyl-polyethylene glycol or octylphenol ethylene oxide), or labeling agents (such as fluorescently-labeled antibodies, enzyme-conjugated antibodies, Pap stain, Giemsa stain, or hematoxylin and eosin stain) may be used.

A solution containing a fluorescent probe may be used to label the target material, thereby providing a fluorescent signal for identification and characterization. The solution containing the fluorescent probe may be added to the suspension before the suspension is added to the vessel, after the suspension is added to the vessel but before centrifugation, or after the suspension has undergone centrifugation. The fluorescent probe includes a fluorescent molecule bound to a ligand. The target material may have a number of different types of surface markers. Each type of surface marker is a molecule, such an antigen, capable of attaching a particular ligand, such as an antibody. As a result, ligands can be used to classify the target material and determine the specific type of target materials present in the suspension by conjugating ligands that attach to particular surface markers with a particular fluorescent molecule. Examples of suitable fluorescent molecules include, but are not limited to, quantum dots; commercially available dyes, such as fluorescein, FITC ("fluorescein isothiocyanate"), R-phycoerythrin ("PE"), Texas Red, allophycocyanin, Cy5, Cy7, cascade blue, Hoechst, DAPI ("4',6-diamidino-2-phenylindole") and TRITC ("tetramethylrhodamine isothiocyanate"); combinations of dyes, such as CY5PE, CY7APC, and CY7PE; and synthesized molecules, such as self-assembling nucleic acid structures. Many solutions may be used, such that each solution includes a different type of fluorescent molecule bound to a different ligand.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:

1. A system comprising:
   a primary vessel comprising an open end and a suspension comprising a target material; and
   a collector comprising
      a main body comprising a first end comprising a cavity and second end comprising an opening,
      a flow regulator to control fluid flow, wherein the flow regulator extends from an apex of the opening to the cavity, and
      a displacement fluid having a density greater than a density of at least a portion of the target material, wherein the displacement fluid is located within the cavity,
   wherein at least the second end of the collector is located within the open end of the primary vessel, and
   wherein the collector extends upwardly from the primary vessel.

2. The system of claim 1, wherein the flow regulator is a valve.

3. The system of claim 2, wherein the valve is closed when centrifugal forces are less than a predetermined amount and the valve is open when centrifugal forces are greater than or equal to a predetermined amount.

4. The system of claim 3, wherein the predetermined amount is 2 g, 5 g, 10 g, 100 g, 1000 g, 2000 g, 2500 g, 3000 g, 5000 g, or 10000 g, and wherein g is the force of gravity.

5. The system of claim 2, wherein the valve is a ball check valve, a diaphragm check valve, a swing check valve, a tilting disk check valve, a lift check valve, or a duckbill valve.

6. The system of claim 1, wherein the flow regulator is a hole comprising a diameter sized and shaped to inhibit fluid flow between the cavity and the concave opening when not undergoing centrifugation.

7. The system of claim 6, wherein the size of the diameter is based on the surface tensions of the displacement fluid and the target material.

8. The system of claim 1, further comprising a float located at a longitudinal position within the primary vessel.

9. The system of claim 1, further comprising a sealing ring located circumferentially around the primary vessel at the same longitudinal position as at least a portion of the float within the primary vessel.

10. The system of claim 1, further comprising a seal between the second end of the collector and an inner wall of the primary vessel to maintain a fluid-tight sealing engagement between the end of the device and inner wall of the primary vessel.

11. The system of claim 1, wherein the displacement fluid is selected from the group consisting of: a solution of colloidal silica particles coated with polyvinylpyrrolidone, a polysaccharide solution, iodixanol, a liquid wax, an oil, a gas, olive oil, mineral oil, silicone oil, immersion oil, mineral oil, paraffin oil, silicon oil, fluorosilicone, perfluorodecalin, perfluoroperhydrophenanthrene, perfluorooctylbromide, ionic liquids, a polymer-based solution, a surfactant, a perfluoroketone, perfluorocyclopentanone, perfluorocyclohexanone, a fluorinated ketone, a hydrofluoroether, a hydrofluorocarbon, a perfluorocarbon, a perfluoropolyether, silicon, a silicon-based liquid, phenylmethyl siloxane, and combinations thereof.

12. A system comprising:
   a primary vessel comprising an open end and a suspension comprising a target material; and
   a collector comprising a main body comprising a first end comprising a cavity and second end comprising an opening, a flow regulator to control fluid flow, wherein the flow regulator extends from an apex of the opening to the cavity, a displacement fluid having a density greater than a density of at least a portion of the target material, wherein the displacement fluid is located within the cavity, and a lid at or near the first end, wherein at least the second end of the collector is located within the open end of the primary vessel.

13. A method comprising the steps of:

providing a primary vessel comprising an open end and a suspension comprising a target material;

inserting a collector into the open end of a primary vessel, the collector comprising:

a main body comprising a first end comprising a cavity and second end comprising an opening, wherein at least the second end is located within the open end of the primary vessel, a flow regulator to control fluid flow, wherein the flow regulator extends from an apex of the opening to the cavity, and wherein the collector extends upwardly from the primary vessel;

adding a displacement fluid to the cavity of the collector, the displacement fluid having a density greater than a density of at least a portion of the target material; and centrifuging the primary vessel, the collector, and the displacement fluid, wherein the displacement fluid flows into the primary vessel via the flow regulator and displaces the at least one portion of the target material from the primary vessel into the cavity of the collector via the flow regulator.

14. The method of claim 13, further comprising the step of: adding a float to the primary vessel prior to the separating step.

15. The method of claim 14, further comprising the steps of:

separating the suspension into fractions by centrifugation after adding the float; and removing at least one of the fractions from the primary vessel.

16. The method of claim 14, further comprising the step of:

forming a seal between the float and the primary vessel after the separating step.

17. The method of claim 13, wherein the flow regulator is a valve.

18. The method of claim 17, wherein the valve is closed when centrifugal forces are less than a predetermined amount and the valve is open when centrifugal forces are greater than or equal to a predetermined amount.

19. The method of claim 13, wherein the flow regulator is a hole comprising a diameter sized and shaped to inhibit fluid flow between the cavity and the concave opening when not undergoing centrifugation.

* * * * *